US009994713B2

(12) United States Patent
Helal

(10) Patent No.: US 9,994,713 B2
(45) Date of Patent: Jun. 12, 2018

(54) FLUORESCENT SCHIFF BASE CONJUGATE CU(II) CHEMOSENSORS AND METHODS THEREOF

(71) Applicant: KING FAHD UNIVERSITY OF PETROLEUM AND MINERALS, Dhahran (SA)

(72) Inventor: Aasif Helal, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 11 days.

(21) Appl. No.: 15/082,808

(22) Filed: Mar. 28, 2016

(65) Prior Publication Data

US 2017/0276607 A1    Sep. 28, 2017

(51) Int. Cl.
| | |
|---|---|
| C09B 26/02 | (2006.01) |
| G01N 33/84 | (2006.01) |
| G01N 33/58 | (2006.01) |
| C09B 11/08 | (2006.01) |
| G01N 33/18 | (2006.01) |

(52) U.S. Cl.
CPC .............. *C09B 26/02* (2013.01); *C09B 11/08* (2013.01); *G01N 33/582* (2013.01); *G01N 33/84* (2013.01); *G01N 33/1813* (2013.01)

(58) Field of Classification Search
CPC .................................................. G01N 21/643
USPC .......................................................... 422/82
See application file for complete search history.

(56) References Cited

PUBLICATIONS

Fasil A. Abebe, Carla Sue Eribal, Guda Ramakrishna, Ekkehard Sinn "A 'turn-on' fluorescent sensor for the selective detection of cobalt and nickel ions in aqueous media" Tetrahedron Letters 52 (2011) 5554-5558 (Year: 2011).*
Ma, P., et al., "A novel fluorescence and surface-enhanced Raman scattering dual-signal probe for pH sensing based on Rhodamine derivative", Dyes and Pigments, vol. 122, pp. 224-230, (2015).
Li, J., et al., "A Novel Rhodamine-Benzimidazole Conjugate as a Highly Selective Turn-on Fluorescent Probe for Fe3+", J. Fluoresc, vol. 21, pp. 2005-2013, (2011).
Gandhi, S., "Turn-on Fluorogenic and chromogenic detection of Fe(III) and its application in living cell imaging", Journal of Luminescence, Total 28 Pages, (Aug. 2013).
Gandhi, S., "Rhodamine based sensor for naked-eye detection and live cell imaging of Fluoride ions", Journal of Materials Chemistry, Total 8 Pages, (Aug. 2013).

\* cited by examiner

*Primary Examiner* — Christine T Mui
*Assistant Examiner* — Emily R. Berkeley
(74) *Attorney, Agent, or Firm* — Oblon, McClelland, Maier & Neustadt, L.L.P.

(57) ABSTRACT

Fluorescent Schiff base compounds comprising a xanthene dye based moiety and an alkyl imidazole moiety. Methods of assessing these fluorescent Schiff base compounds as fluorescent probes for metal ions in $Cu^{2+}$ chemosensing applications, methods of preparing the fluorescent Schiff base compounds and methods of detecting $Cu^{2+}$ ions with the same are also provided.

20 Claims, 13 Drawing Sheets

Compound 1:
$\lambda_{max} = 342$ nm, $\lambda_{em} = 525$ nm

Compound 1 + $Cu^{2+}$:
$\lambda_{max} = 502$ nm, 342 nm, $\lambda_{em} = 0$

Compound 1:
$\lambda_{max} = 342$ nm, $\lambda_{em} = 525$ nm

Compound 1 + $Cu^{2+}$:
$\lambda_{max} = 502$ nm, 342 nm, $\lambda_{em} = 0$

FLUORESCENT SCHIFF BASE CONJUGATE CU(II) CHEMOSENSORS AND METHODS THEREOF

BACKGROUND OF THE INVENTION

Technical Field

The present disclosure relates to fluorescent Schiff base compounds as well as methods for their synthesis. In addition, the present disclosure relates to applications of these compounds as fluorescent probes for chemical sensing of metal ions such as $Cu^{2+}$.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Fluorescent chemosensors are highly valuable as they provide accurate detection of heavy metal ions with high sensitivity, specificity and simplicity at a low cost and afford the rapid tracking of analytes in biological, toxicological and environmental samples [Silva, A. P.; de Nimal Gunaratne, H. Q.; Gunnlaugsson, T.; Huxley, A. J. M.; McCoy, C. P.; Rademacher, J. T.; Rice, T. E. *Chem. Rev.* 1997, 97, 1515.; and Valeur, B.; Leray, I. *Coord. Chem. Rev.* 2000, 205, 3.; and Lee, C. H.; Miyaji, H.; Yoon, D. W.; Sessler, J. L. *Chem. Commun.* 2008, 24.; and Yoon, J.; Kim, S. K.; Singh, N. J.; Kim, K. S. *Chem. Soc. Rev.* 2006, 35, 355.; and Chung, S. Y.; Nam, S. W.; Lim, J.; Park, S.; Yoon, *J. Chem. Commun.* 2009, 2866.—each incorporated herein by reference in its entirety]. Copper is the third most essential element for life after iron and zinc [Lippard, S. J.; Berg, J. M. Principles of Bioinorganic Chemistry, University Science Books, Mill Valley, C A, 1994.—incorporated herein by reference in its entirety]. Copper effects are diverse and wide-ranging as this metal serves as an essential cofactor for numerous redox enzymes that are involved in critical processes such as respiration (e.g. cytochrome c oxidase), electron transfer/substrate oxidation and iron uptake (e.g. ceruloplasmin), pigmentation (e.g. tyrosinase), neurotransmitter synthesis and metabolism (e.g. dopamine β-hydroxylase, peptidylglycine) and handling of dietary amines (e.g. copper amine oxidases) [Ferguson-Miller, S.; Babcock, G. T. *Chem. Rev.* 1996, 96, 2889.; and Ishida, S.; Andreux, P.; Poitry-Yamate, C.; Auwerx, J.; Hanahan, D. *Proc. Natl. Acad. Sci. U S. A.* 2013, 110, 19507.; and Ghosh, A.; Trivedi, P. P.; Timbalia, S. A.; Griffin, A. T.; Rahn, J. J.; Chan, S. S.; Gohil, V. M.; *Hum. Mol. Genet.*, 2014, 23, 3596.; and Hellman, N. E.; Gitlin, J. D. *Annu. Rev. Nutr.* 2002, 22, 439.; and Olivares, C.; Solano, F. *Pigm. Cell Melanoma Res.* 2009, 22, 750.; and Dawkes, H. C.; Phillips, S. E. V. *Curr. Opin. Struct. Biol.* 2001, 11, 666.; and Klinman, J. P. *Biochim. Biophys. Acta* 2003, 1637, 131.—each incorporated herein by reference in its entirety]. On the other hand, unregulated overloading of copper from copper polluted water results in human genetic disorders like Menkes and Wilson's diseases; neurodegenerative diseases such as Alzheimer's, Parkinson's, prion, and Huntington's disease and familial amyotrophic lateral sclerosis, and metabolic disorders such as obesity and diabetes [Kaler, S. G. *Nat. Rev. Neurol.* 2011, 7, 15.; and Lutsenko, S. *Biochem. Soc. Trans.* 2008, 36, 1233. (c) Huster, D. *Ann. N. Y. Acad. Sci.* 2014, 1314, 37.; and Que, E. L.; Domaille, D. W.; Chang, C. *J. Chem. Rev.* 2008, 108, 1517.; and Ayton, S.; Lei, P.; Bush, A. I. *Free Radical Biol. Med.* 2013, 62, 76.; and Savelieff, M. G.; Lee, S.; Liu, Y.; Lim, M. H. *ACS Chem. Biol.* 2013, 8, 856.; and Matlack, K. E.; Tardiff, D. F.; Narayan, P.; Hamamichi, S.; Caldwell, K. A.; Caldwell, G. A.; Lindquist, S. *Proc. Natl. Acad. Sci. U S. A.* 2014, 111, 4013.; and Vonk, W. I.; Kakkar, V.; Bartuzi, P.; Jaarsma, D.; Berger, R.; Hofker, M. H.; Klomp, L. W.; Wijmenga, C.; Kampinga, H. H.; van de Sluis, B. *PLoS One* 2014, 9, 92408.; and McDonald, A. J.; Dibble, J. P.; Evans, E. G.; Millhauser, G. L. *J. Biol. Chem.* 2014, 289, 803.; and Xiao, G.; Fan, Q.; Wang, X.; Zhou, B. *Proc. Natl. Acad. Sci. U S. A.* 2013, 110, 14995.; and Burkhead, J. L.; Lutsenko, S. in Lipid Metabolism, ed. R. V. Baez, InTech, 2013, DOI: 10.5772/51819.; and Engle, T. E. *J. Anim. Sci.* 2011, 89, 591.; and Nielsen, T. S.; Jessen, N.; Jorgensen, J. O.; Moller, N.; Lund, S. J. *Mol. Endocrinol.* 2014, 52, R199.—each incorporated herein by reference in its entirety]. More recently, copper has also been found to regulate cancers [Brady, D. C.; Crowe, M. S.; Turski, M. L.; Hobbs, G. A.; Yao, X.; Chaikuad, A.; Knapp, S.; Xiao, K.; Campbell, S. L.; Thiele, D. J.; Counter, C. M. *Nature* 2014, 509, 492.—incorporated herein by reference in its entirety].

Furthermore, due to its widespread use in various industries $Cu^{2+}$ is a significant environmental pollutant. The World Health Organization (WHO) has set the safe limit of copper in drinking water at 2 ppm (31.5 μM) [WHO. WHO guidelines values for chemicals that are of health significance in drinking water, Guidelines for Drinking Water Quality, Geneva, 3rd edn, 2008.—incorporated herein by reference in its entirety]. Thus, the development of chemosensors for the discriminatory and fast recognition and monitoring of copper is in great demand [Krämer, R. *Angew. Chem., Int. Ed.* 1998, 37, 772.—incorporated herein by reference in its entirety]. These chemosensors necessitate a high sensitivity, a low detection limit and a quick response. Current methods for copper screening, including atomic absorption spectrometry (AAS), inductively coupled plasma mass spectrometry (ICP-MS), inductively coupled plasma atomic emission spectrometry (ICP-AES), total reflection X-ray fluorimetry (TXRF) and anodic stripping voltammetry (ASV) often require expensive and sophisticated instrumentation or complex sample preparation steps [Pourreza, N.; Hoveizavi, R. *Anal. Chim. Acta.* 2005, 549, 124.; and Becker, J. S; Zoriy, M. V; Pickhardt, C.; Palomero-Gallagher, N.; Zilles, K. *Anal. Chem.* 2005, 77, 3208.; and Otero-Romaní, J.; Moreda-Piñieiro, A.; Bermejo-Barrera, A.; Bermejo-Barrera, P. *Anal. Chim. Acta.* 2005, 536, 213.; and Becker, J.; Zoriy, M.; Pickhardt, C.; Palomero-Gallagher, N.; Zilles, K. *Anal. Chem.* 2005, 77, 3208.; and Twining, B.; Baines, S.; Fisher, N.; Jacobsen, C.; Maser, J. *J. Phys. IV,* 2003, 104, 435.—each incorporated herein by reference in its entirety]. Many traditional methods of detecting copper using small molecular chemosensors based on a rhodamine Schiff base, a novel rhodamine hydrazine, a 1,8-naphthyridyl moiety, and a novel coumarin based groups are also reported [Yang, Z.; She, M.; Zhang, J.; Chen, X. X.; Huang, Y. Y.; Zhu, H. Y.; Liu, P.; Li, J. L.; Shi, Z. *Sens. Actuators. B* 2013, 176, 482.; and Lee, H. Y.; Swamy, K. M. K.; Jung, J. Y.; Kim G.; Yoon, J. *Sens. Actuators. B* 2013, 182, 530.; and Yu, M. M.; Li, Z. X.; Wei, L. H.; Wei, D. H.; Tang, M. S. *Org. Lett.* 2008, 10, 5115.; and Jung, H. S.; Kwon, P. S.; Lee, J. W.; Kim, J. I.; Hong, C. S.; Kim, J. W.; Yan, S. H.; Lee, J. Y.; Lee, J. H.; Joo, T.; Kim, J. S. *J. Am. Chem. Soc.* 2009, 131, 2008.—each incorporated herein by reference in its entirety].

Among the highly fluorescent dyes, the xanthene scaffold based rhodamine and fluorescein dyes have attracted considerable interest from chemists due to their excellent photophysical properties [Zheng, H.; Zhan, X.-Q.; Biana, Q.-N.; Zhanga, X.-J. Chem. Commun., 2013, 49, 429.—incorporated herein by reference in its entirety]. The fluorescein framework is useful for the construction of fluorescent chemosensors due to its favorable properties such as easy synthesis and functionalization, excitation and emission wavelengths in the visible region with a high fluorescence quantum yield, excellent biocompatibility, high molar extinction coefficient, high photostability and water solubility [Duan, Y.; Liu, M.; Sun, W.; Wang, M.; Liu, S.; Li, Q. Mini. Rev. Org. Chem. 2009, 6, 35.; and Zhou, Y.; Li, J.; Chu, K.; Liu, K.; Yao, C.; Li, J. Chem. Commun. 2012, 48, 4677.; and Xiong, X. Q.; Song, F. L.; Chen, G. W.; Sun, W.; Wang, J. Y.; Gao, P. Chem. Eur. J. 2013, 19, 6538.; and An, J. M.; Yan, M. H.; Yang, Z. Y.; Li, T. R.; Zhou, Q. X. Dyes Pigments 2013, 99, 1.; and Kim, H. J.; Park, J. E.; Choi, M. G.; Ahn, S.; Chang, S. K. Dyes Pigments 2010, 84, 54.; and Egawa, T.; Koide, Y.; Hanaoka, K.; Komatsu, T.; Teraia, T.; Nagano, T. Chem. Commun. 2011, 47, 4162.; and Ueno, T.; Urano, Y.; Setsukinai, K.; Takakusa, H.; Kojima, H.; Kikuchi, K.; Ohkubo, K.; Fukuzumi, S.; Nagano, T. J. Am. Chem. Soc. 2004, 126, 14079.—each incorporated herein by reference in its entirety].

The imidazole scaffold has been widely used as a building block in many fields, such as medicine, biology, electronic and optical materials, ionic liquids, and as chemosensors [Bellina, F.; Cauteruccio, S.; Montib, S.; Rossi, R. Bioorg. Med. Chem. Lett. 2006, 16, 5757.; and Bando, T.; Sugiyama, H. Acc. Chem. Res. 2006, 39, 935.; and Sun, Y. F.; Cui, Y. P. Dyes Pigment 2009, 81, 27.; and Peter, W.; Wilhelm, K. Angew Chem Int Ed 2000, 39, 3772.; and Kumar, A.; Kim, H.-S. Spectrochim. Acta. A 2015, 148, 250.; and Kumar, A.; Ghosh, M. K.; Choi, C.-H.; Kim, H.-S. RSC Adv. 2015, 5, 23613.; and Kumar, A.; Kim, H.-S. New J Chem. 2015, 39, 2935.; and Hens, A.; Maity, A.; Rajak, K. K. Inorg. Chim. Acta 2014, 423, 408.—each incorporated herein by reference in its entirety]. Imidazole is a π-electron rich heteroaromatic molecule with the density of electrons located more on the nitrogen atoms. Moreover, imidazole shows excellent coordination properties toward metal ions [Li, Z. Y.; Lin, Y.; Xia, J. L.; Zhang, H.; Fan, F. Y; Zeng, Q. B. Dyes Pigment 2011, 90, 245.—incorporated herein by reference in its entirety]. Various substituted imidazoles form complexes with many metal ions in which the donation is realized by the pyridinic nitrogen atom. Moreover, due to its biological activity and available sites for further functionalization imidazole derivatives have also been applied in environmental monitoring, industrial process control, metalloneurochemistry, and biomedical diagnostics.

The syntheses of Schiff bases are usually simple and easy and they are also well known as good ligands for metal ions. Thus Schiff base derivatives with an incorporated fluorescent moiety as a signaling unit and imidazole as a binding unit are appealing tools for the optical sensing of metal ions [Fasil, A.; Abebe, C.; Eribal, S.; Ramakrishna, G.; Sinn, E. Tetrahedron Lett. 2011, 52 5554.; and Sivaraman, G.; Chellappa, D. J. Mater. Chem. B 2013, 1, 5768.; and Ding, J.; Yuan, L.; Gao, L.; Chen, J. J. Lumin. 2012, 132, 1987.; and Sivaraman, G.; Sathiyaraja, V.; Chellappa, D. I. Lumin. 2014, 145, 480.—each incorporated herein by reference in its entirety].

In view of the forgoing, one object of the present disclosure is to provide fluorescent Schiff base compounds, such as fluorescein-imidazole conjugates, with reversible highly selective chromogenic and fluorogenic responses for sensing of metal ions, such as Cu(II). An additional aspect of the present disclosure is methods for forming these Schiff base compounds as well as methods for detecting and quantifying metal ions, such as Cu(II) employing the fluorogenic responses.

BRIEF SUMMARY OF THE INVENTION

According to a first aspect, the present disclosure relates to a fluorescent Schiff base of formula (I)

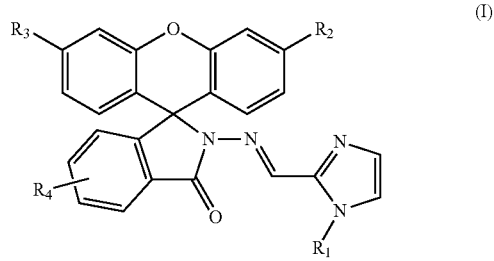

(I)

or a salt, solvate, tautomer or stereoisomer thereof wherein i) $R_1$ is an optionally substituted alkyl, optionally substituted cycloalkyl, or optionally substituted aryl, ii) $R_2$ and $R_3$ are independently —OH, —$NH_2$, —$OR_5$, —$NHR_5$, —$NR_5R_5$, iii) $R_4$ is —H, —F, —Br, —CN, —OH, —$OR_5$, —$NO_2$, —$NH_2$, —$NHR_5$, —$NR_5R_5$, and each $R_5$ is independently an optionally substituted alkyl, optionally substituted cycloalkyl, or optionally substituted aryl.

In one embodiment, $R_1$ is —$CH_3$, $R_2$ is —OH, $R_3$ is —OH, and each $R_4$ is —H and fluorescent Schiff base of formula (I) is

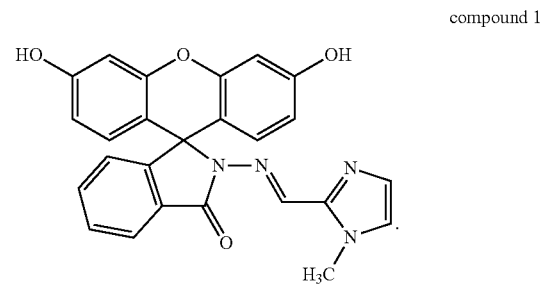 [SMILES: Cn1ccnc1/C=N/N1C(=O)c2ccccc2C12c1ccc(O)cc1Oc1cc(O)ccc12]

compound 1

In one embodiment, the fluorescent Schiff base has a fluorescence with an emission peak centered at 515-535 nm at an excitation wavelength of 490-510 nm and has an ultraviolet visible absorption with an absorption peak centered at 330-350 nm.

In one embodiment, upon binding of the fluorescent Schiff base with one or more $Cu^{2+}$ ions the ultraviolet visible absorption with an absorption peak centered at 330-350 nm decreases in intensity synchronously to an increasing ultraviolet visible absorption with an absorption peak centered at 490-510 nm.

In one embodiment, upon binding of the fluorescent Schiff base with one or more $Cu^{2+}$ ions the fluorescence with an emission peak centered at 515-535 nm at an excitation wavelength of 490-510 nm is quenched and/or inhibited.

In one embodiment, the fluorescent Schiff base binds with one or more $Cu^{2+}$ ions by monodentate coordination, bidentate chelation, or tridentate chelation to the $Cu^{2+}$ ion to form a metal ion complex.

In one embodiment, the fluorescent Schiff base has a $Cu^{2+}$ binding constant in the range of $0.5\times10^7$ $L\cdot mol^{-1}$ to $1.5\times10^7$ $L\cdot mol^{-1}$ as calculated from fluorescence titration.

According to a second aspect, the present disclosure relates to a process for producing the fluorescent Schiff base comprising i) refluxing a fluorescein or rhodamine based compound with hydrazine to form a fluorescein or rhodamine based hydrazide and ii) refluxing the fluorescein or rhodamine based hydrazide with a N-alkylamidazole-2-carboxaldehyde to form the fluorescent Schiff base.

According to a third aspect, the present disclosure relates to a method for detecting and quantifying $Cu^{2+}$ ions in a fluid sample comprising i) contacting the fluid sample with the fluorescent Schiff base and ii) measuring fluorescence emission at 515-535 nm with an excitation wavelength of 490-510 nm to determine a concentration of $Cu^{2+}$ ions in the fluid sample, wherein during the contacting the fluorescent Schiff base binds to the $Cu^{2+}$ ions at a molar ratio of 1:1 and quenches and/or inhibits the fluorescence emission.

In one embodiment, the binding of the fluorescent Schiff base to the $Cu^{2+}$ ions further results in an ultraviolet visible absorption with an absorption peak centered at 490-510 nm.

In one embodiment, the binding of the fluorescent Schiff base to the $Cu^{2+}$ ions is a chemically reversible process and the introduction of a chelator restores the fluorescence emission centered at 515-535 nm.

In one embodiment, the method further comprises measuring the fluorescence emission of a plurality of calibration fluid samples to obtain a calibration curve, wherein the plurality of calibration fluid samples comprise different known concentrations of $Cu^{2+}$ ions.

In one embodiment, the fluid sample has a pH in the range of 4.5 to 10.5.

In one embodiment, the fluorescent Schiff base is present at a concentration of 0.1-25 μM during the measuring.

In one embodiment, the method has a $Cu^{2+}$ detection lower limit of 0.01-0.05 μM without interference from one or more additional metal ions.

In one embodiment, the one or more additional metal ions are selected from the group consisting of $Ag^{2+}$, $Pb^{2+}$, $Ca^{2+}$, $Ni^{2+}$, $Co^{2+}$, $K^+$, $Zn^{2+}$, $Al^{3+}$, $Fe^{3+}$, $Fe^{2+}$, $Na^+$, $Cd^{2+}$, $Mg^{2+}$, $Hg^{2+}$, $Rb^+$, and $Cs^+$.

In one embodiment, fluid sample comprises greater than 10% v/v of water as a solvent and is at least one selected from the group consisting of contaminated water, a consumable good, and a bodily fluid.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
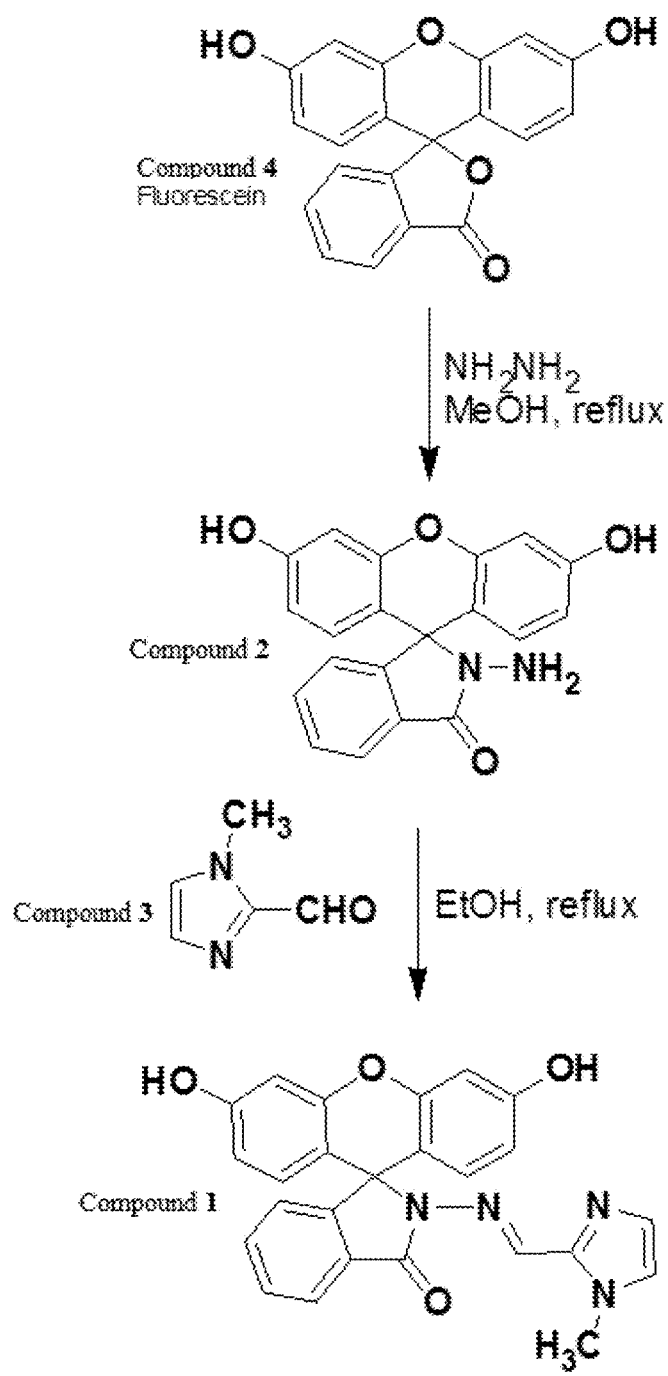
FIG. 1 is a synthetic scheme for the production of a fluorescein-N-methylimidazole conjugate based compound of formula (I), compound 1, from the reaction of fluorescein compound 4 with hydrazine to form fluorescein hydrazide compound 2 and the subsequent reaction of fluorescein hydrazide compound 2 with N-methylimidazole-2-carbaldehyde compound 3.

Referring now to the drawings.

According to a first aspect, the present disclosure relates to a fluorescent Schiff base of formula (I)

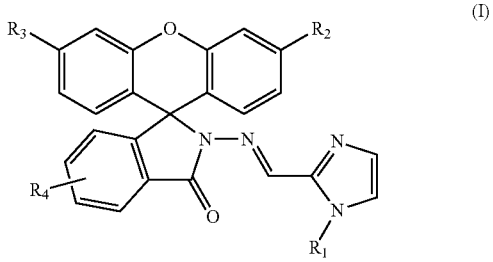

(I)

or a salt, solvate, tautomer or stereoisomer thereof wherein
i) $R_1$ is an optionally substituted alkyl, optionally substituted cycloalkyl, or optionally substituted aryl, preferably $R_1$ is —$CH_3$ or —$CH_2CH_3$ ii) $R_2$ and $R_3$ are independently —OH, —$NH_2$, —$OR_5$, —$NHR_5$, —$NR_5R_5$, preferably $R_2$ and $R_3$ are —OH or —$NH_2$ iii) $R_4$ is —H, —F, —Cl, —Br, —CN, —OH, —$OR_5$, —$NO_2$, —$NH_2$, —$NHR_5$, —$NR_5R_5$, and each $R_5$ is independently an optionally substituted alkyl, optionally substituted cycloalkyl, or optionally substituted aryl, preferably $R_4$ is —H.

As used herein, a Schiff base refers to a compound with a functional group that contains a carbon-nitrogen double bond with the nitrogen atom connected to a non-hydrogen atom or group. A Schiff base is a compound with the general structure ($R_2$C=NR') wherein R'≠H. They can be considered a sub-class of imines, being either secondary ketimines or secondary aldimines, depending on their structure. The term is often synonymous with azomethine which refers specifically to secondary aldimines (i.e. R—CH=NR', wherein R' H). A number of special naming systems exist for these compounds. The term Schiff base is normally applied to these compounds when they are being used as ligands to form coordination complexes with metal ions. Such complexes do occur naturally, for instance in Corrin, but the majority of Schiff bases are artificial and are used for many important functions including catalysis.

As used herein, the terms "compound" and complex" refer to a chemical entity, whether in the solid, liquid or gaseous phase, as well as in a crude mixture or purified and isolated form. The chemical transformations and/or reactions described herein are envisaged to proceed via standard laboratory and experimental techniques in regard to performing the reactions as well as standard purification, isolation and characterization protocols know to those of ordinary skill in the art.

As used herein, the term "salts" refers to derivatives of the disclosed compounds, wherein the parent compound is modified by making acid or base salts thereof. Exemplary salts include, but are not limited to, mineral or organic acids salts of basic groups such as amines, and alkali or organic salts of acidic groups such as carboxylic acid. The salts include, but are not limited to, the conventional non-toxic salts formed, for example, from non-toxic inorganic or organic acids. Exemplary conventional non-toxic salts include those derived from inorganic acids, including, but not limited to, hydrochloric, hydrobromic, sulfuric, sulfamic, phosphoric, and nitric; and those derived from organic acids including, but not limited to, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic and mixtures thereof and the like. Further, salts of carboxylic acid compounds may include cations such as lithium, sodium, potassium, magnesium, quaternary ammonium, and the like. The salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, on in a mixture of the two; generally non-aqueous media like ether, ethyl acetate, ethanol, isopropanol, or acetonitrile are preferred.

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvates include, but are not limited to, hydrates, ethanolates, methanolates, isopropanolates and mixtures thereof. Methods of solvation are generally known to those of ordinary skill in the art.

As used herein, the term "tautomer" refers to constitutional isomers of organic compounds that readily convert by the chemical reaction of tautomerization or tautomerism. The reaction commonly results in the formal migration of a hydrogen atom or proton, accompanied by a switch of a single bond and adjacent double bond. Tautomerism is a special case of structural isomerism and because of the rapid interconversion; tautomers are generally considered to be the same chemical compound. In solutions in which tautomerization is possible, a chemical equilibrium of the tautomers will be reached. The exact ratio of the tautomers depends on several factors including, but not limited to, temperature, solvent and pH. Exemplary common tautomeric pairs include, but are not limited to, ketone and enol, enamine and imine, ketene and ynol, nitroso and oxime, amide and imidic acid, lactam and lactim (an amide and imidic acid tautomerism in heterocyclic rings), enamine and enamine and anomers of reducing sugars.

Prototropy or prototropic tautomerism refers to the relocation of a proton. Prototropy may be considered a subset of acid base behavior. Prototropic tautomers are sets of isomeric protonation states with the same empirical formula and total charge. Tautomerizations may be catalyzed by bases (deprotonation, formation of an enolate or delocalized anion, and protonation at a different position of the anion) and/or acids (protonation, formation of a delocalized cation and deprotonation at a different position adjacent to the cation). Two additional subcategories of tautomerization include annular tautomerism, wherein a proton can occupy two or more positions of a heterocyclic system, and ring-chain tautomerism, wherein the movement of a proton is accompanied by a change from an open structure to a ring. Valence tautomerism is a type of tautomerism in which single and/or double bonds are rapidly formed and ruptured, without migration of atoms or groups. It is distinct from prototropic tautomerism, and involves processes with rapid reorganization of bonding electrons, such as open and closed forms of certain heterocycles, such as azide-tetrazole or mesoionic munchnone-acylamino ketene. Valence tautomerism requires a change in molecular geometry unlike canonical resonance structures or mesomers. In terms of the present disclosure, the tautomerism may refer to prototropic tautomerism, annular tautomerism, ring-chain tautomerism, valence tautomerism, or mixtures thereof.

As used herein, the term "stereoisomer" refers to isomeric molecules that have the same molecular formula and sequence of bonded atoms (i.e. constitution), but differ in the three-dimensional orientations of their atoms in space. This contrasts with structural isomers, which share the same molecular formula, but the bond connection or their order differs. By definition, molecules that are stereoisomers of each other represent the same structural isomer. Enantiomers are two stereoisomers that are related to each other by reflection, they are non-superimposable mirror images. Every stereogenic center in one has the opposite configuration in the other. Two compounds that are enantiomers of each other have the same physical properties, except for the direction in which they rotate polarized light and how they interact with different optical isomers of other compounds. Diastereomers and stereoisomers are not related through a reflection operation, they are not mirror images of each other. These include meso compounds, cis- and trans- (E- and Z-) isomers, and non-enantiomeric optical isomers. Diastereomers seldom have the same physical properties. In terms of the present disclosure, stereoisomers may refer to enantiomers, diastereomers or both.

Conformers (rotamers), or conformational isomerism refers to a form of isomerism that describes the phenomenon of molecules with the same structural formula but with different shapes due to rotations about one or more bonds. Different conformations can have different energies, can usually interconvert, and are very rarely isolatable. There are some molecules that can be isolated in several conformations. Atropisomers are stereoisomers resulting from hindered rotation about single bonds where the steric strain barrier to rotation is high enough to allow for the isolation of the conformers. In terms of the present disclosure, stereoisomers may refer to conformers, atropisomers, or both.

In terms of the present disclosure, geometric and stereoisomers of the double bonds (N=N, C=N), ring systems, stereogenic centers, and the like can all be present in the compounds, and all such stable isomers are contemplated in the present disclosure. Cis- and trans- (or E- and Z-) stereoisomers of the compounds of the present disclosure wherein rotation about the double bond is restricted, keeping the substituents fixed relative to each other, are described and may be isolated as a mixture of isomers or as separated isomeric forms. S- and R- (or L- and D-) stereoisomers of the compounds of the present disclosure are described and may be isolated as a mixture of isomers or as separated isomeric forms. All processes or methods used to prepare compounds of the present disclosure and intermediates made therein are considered to be part of the present disclosure. When stereoisomeric products are prepared, they may be separated by conventional methods, for example by chromatography, fractional crystallization, or use of a chiral agent.

The present disclosure is further intended to include all isotopes of atoms occurring in the present compounds. Isotopes include those atoms having the same atomic number but different mass numbers. By way of general example, and without limitation, isotopes of hydrogen include deuterium and tritium. Isotopes of carbon include $^{13}C$ and $^{14}C$. Isotopically labeled compounds of the invention can generally be prepared by conventional techniques known to those of ordinary skill in the art or by processes and methods analogous to those described herein, using an appropriate isotopically labeled reagent in place of the non-labeled reagent otherwise employed.

As used herein, the term "substituted" refers to at least one hydrogen atom that is replaced with a non-hydrogen group, provided that normal valencies are maintained and that the substitution results in a stable compound. Substitution as indicated by $R_4$ in a compound of formula (I) indicates optional substitution of one or more of the hydrogens of the fused phenyl C—H bonds. When a substituent is noted as "optionally substituted", the substituents are selected from the exemplary group including, but not limited to, halo, hydroxyl, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl or arylalkyl), alkanylamino, aroylamino, aralkanoylamino, substituted alkanoylamino, substituted arylamino, substituted aralkanoylamino, thiol, alkylthio, arylthio, arylalkylthio, alkylthiono, arylthiono, aryalkylthiono, alkylsulfonyl, arylsulfonyl, arylalkylsulfonyl, sulfonamide (e.g. —SO$_2$NH$_2$), substituted sulfonamide, nitro, cyano, carboxy, carbamyl (e.g. —CONH$_2$), substituted carbamyl (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted hetercyclyl and mixtures thereof and the like.

As used herein, the term "alkyl" unless otherwise specified, refers to both branched and straight chain saturated aliphatic primary, secondary, and/or tertiary hydrocarbons of typically $C_1$ to $C_{10}$, and specifically includes, but is not limited to, methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. As used herein, the term optionally includes substituted alkyl groups. Exemplary moieties with which the alkyl group can be substituted may be selected from the group including, but not limited to, hydroxyl, amino, alkylamino, arylamino, alkoxy, aryloxy, nitro, cyano, sulfonic acid, sulfate, phosphonic acid, phosphate, or phosphonate or mixtures thereof. The substituted moiety may be either protected or unprotected as necessary, and as known to those of ordinary skill in the art.

As used herein, the term "cycloalkyl" refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure.

As used herein, the term "aryl" unless otherwise specified refers to functional groups or substituents derived from an aromatic ring including, but not limited to, phenyl, biphenyl, napthyl, thienyl, and indolyl. In certain embodiments, the term aryl, either alone or in combination with another radical, means a carbocyclic aromatic monocyclic group containing 6 carbon atoms which may be further fused to a second 5- or 6-membered carbocyclic group which may be aromatic, saturated, or unsaturated. As used herein, the term optionally includes both substituted and unsubstituted moieties. Exemplary moieties with which the aryl group can be substituted may be selected from the group including, but not limited to, hydroxyl, amino, alkylamino, arylamino, alkoxy, aryloxy, nitro, cyano, sulfonic acid, sulfate, phosphonic acid, phosphate or phosphonate or mixtures thereof. The substituted moiety may be either protected or unprotected as necessary, and as known to those of ordinary skill in the art.

In a preferred embodiment, the fluorescent Schiff base of formula (I) can be viewed as a conjugate or hybrid of a xanthene dye based hydrazine moiety and a N-alkylimidazole moiety conjugated via a nitrogen-nitrogen bond to a spirolactam moiety of the xanthene dye based hydrazine moiety. As used herein, xanthene (9H-xanthene, 10H-9-oxaanthracene) refers to a moiety of chemical formula $C_{13}H_{10}O$. Derivatives of xanthene are commonly referred to collectively as xanthenes, and among other uses is the basis for a class of dyes including fluorescein, eosin and rhodamine. In some embodiments, the xanthene moiety is fluorescein based and may include, but is not limited to, fluorescein, fluorescein isothiocyanate, succinimidyl ester fluorescein (NHS-fluorescein), carboxyfluorescein, carboxy fluorescein succinimidyl ester, pentafluorophenyl esters (PFP), tetrafluorophenyl esters (TFP), protected fluorescein (6-FAM phosphoramidite and the like. In some embodiments, fluorescein derivatives can be prepared from phthalic anhydride and resorcinol in the presence of zinc chloride via a Friedel-Crafts reaction, or alternatively using methanesulfonic acid as a Bronsted acid catalyst. In some embodiments, the xanthene moiety is rhodamine based and may include, but is not limited to, rhodamine, rhodamine B, rhodamine 6G, rhodamine 123, carboxyltetramethyl rhodamine (TAMRA), tetramethyl rhodamine (TMR), its isothiocyanate derivative (TRITC), sulforhodamine 101 (and its sulfonyl chloride), rhodamine red, isothiocyanate modified rhodamine and the like.

In certain embodiments, it is equally envisaged that the N-alkylimidazole moiety of the fluorescent Schiff base of formula (I) may be replaced with other suitably substituted aromatic heterocyclic groups, the only requirement is that the suitably substituted aromatic heterocyclic groups be able to coordinate to metal ions (such as copper) in the manner described herein as the heteroatom is essential to this coordination. As used herein, the term "aromatic heterocyclic group" is intended to mean stable monocyclic and polycyclic aromatic hydrocarbons that include at least one heteroatom ring member such as sulfur, oxygen and/or nitrogen. Aromatic heterocyclic groups include, but are not limited to, without limitation pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, inolinyl, benzodioxolanyl, and benzodioxane. Further, any constituent nitrogen and sulfur heteroatoms may optionally be oxidized (i.e. N→O and $S(O)_p$, wherein p is 0, 1 or 2).

In one embodiment, $R_1$ is —$CH_3$, $R_2$ is —OH, $R_3$ is —OH, and each $R_4$ is —H and fluorescent Schiff base of formula (I) is

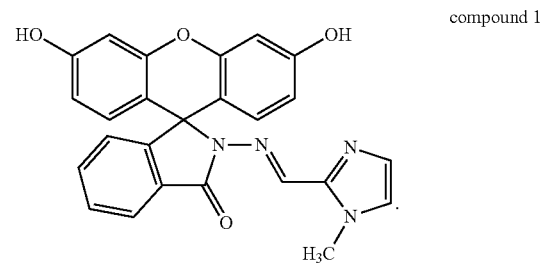 [SMILES: Cn1ccnc1/C=N/N1C(=O)c2ccccc2C12c1ccc(O)cc1Oc1cc(O)ccc12]

compound 1

In other embodiments, the fluorescent Schiff base of formula (I) is

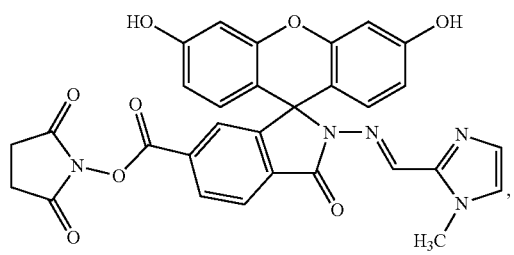

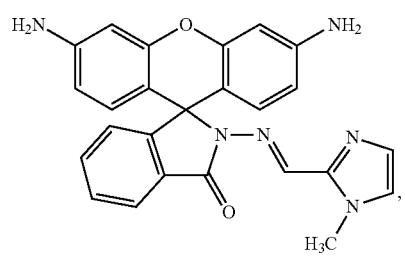

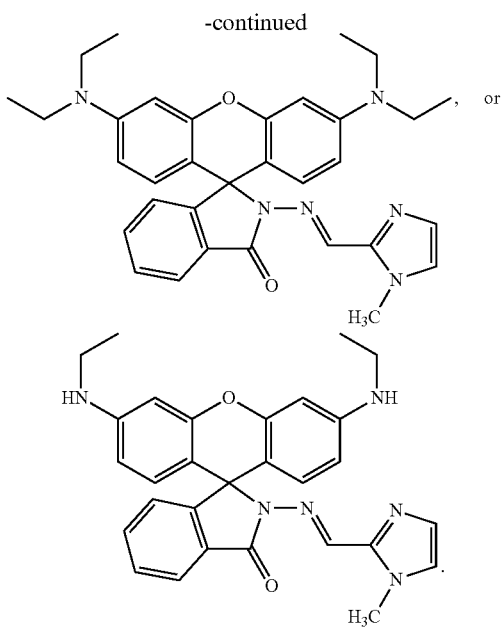
, or

In a certain embodiments, a structural evaluation study may also be done for the synthesized fluorescent Schiff base compounds of formula (I) of the present disclosure. The disclosed compounds may characterized and assess for purity with known spectroscopic techniques such as infrared (IR), mass spectrometry (MS), nuclear magnetic resonance (NMR) spectroscopic studies or other known instrumentation common to those of ordinary skill in the art. In addition, stock solutions of these compounds may be prepared for these studies.

As used herein, ultraviolet-visible spectroscopy or ultraviolet-visible spectrophotometry (UV-Vis or UV/Vis) refers to absorption spectroscopy or reflectance spectroscopy in the ultraviolet-visible spectral region. This means it uses light in the visible and adjacent (near-UV and near-infrared) ranges. The absorption or reflectance in the visible range directly affects the perceived color of the chemicals involved. In this region of the electromagnetic spectrum, molecules undergo electronic transitions. Molecules containing π-electrons or non-bonding electrons (n-electrons) can absorb the energy in the form of ultraviolet or visible light to excite these electrons to higher anti-bonding molecular orbitals. The more easily excited the electrons (i.e. the lower the energy gap between the HOMO and the LUMO), the longer the wavelength of light it can absorb. In a preferred embodiment, the fluorescent Schiff base of formula (I) has an ultraviolet visible absorption with an absorption peak centered at 330-350 nm, preferably 335-348 nm, preferably 338-346 nm, preferably 340-344 nm, or about 342 nm. In one embodiment, this absorption may be ascribed to that of the xanthene moiety of the compound of formula (I). In addition, the lack of absorption in the visible region suggests the fluorescent Schiff base of formula (I) is persisting as the lactam form. This technique is complementary to fluorescence spectroscopy, in that fluorescence deals with transitions from the excited state to the ground state, while absorption measures transitions from the ground state to the excited state.

As used herein, fluorescence is the emission of light by a substance that has absorbed light or other electromagnetic radiation. It is a form of luminescence. In most cases, the emitted light has a longer wavelength, and therefore lower energy, than the absorbed radiation. However, unlike phosphorescence, where the substance would continue to glow and emit light for some time after the radiation source has been turned off, fluorescent materials would cease to glow immediately upon removal of the excitation source. Hence, it is not a persistent phenomenon. Fluorescence occurs when an orbital electron of a molecule, atom, or nanostructure relaxes to its ground state by emitting a photon from an excited singlet state. In general, hv is a generic term for photon energy with h referring to Planck's constant and v referring to a frequency of light, the specific frequencies of exciting and emitted light are dependent on the particular system. In general, excitation is represented as $S_0 + h\nu_{ex} \rightarrow S_1$ and fluorescence (emission) is represented as $S_1 \rightarrow S_0 + h\nu_{em} +$ heat, wherein $S_0$ is the ground state of the fluorophore (fluorescent molecule), and $S_1$ is the first (electronically) excited singlet state. A molecule in $S_1$ can relax by various competing pathways. It can undergo non-radiative relaxation in which the excitation energy is dissipated as heat (vibrations) to the solvent. Exited organic molecules can also relax via conversion to a triplet state, which may subsequently relax via phosphorescence, or by a secondary non-radiative relaxation step. Relaxation from $S_1$ can also occur through interaction with a second molecule through fluorescence quenching. In most cases, the emitted light has a longer wavelength, and therefore lower energy, then the absorbed radiation in a phenomenon known as the Stokes shift. However, when the absorbed electromagnetic radiation is intense, it is possible for one electron to absorb two photons and this two photon absorption can lead to emission of radiation having a shorter wavelength than the absorbed radiation. The emitted radiation may also be of the same wavelength as the absorbed radiation, termed "resonance fluorescence". Molecules that are excited through light absorption or via a different process (e.g. as the product of a reaction) can transfer energy to a second sensitized molecule, which is converted to its excited state and can then fluoresce.

In a preferred embodiment, the fluorescent Schiff base of formula (I) has a fluorescence with an emission peak centered at 515-535 nm, preferably 518-532 nm, preferably 520-530 nm, preferably 522-528 nm, or about 525 nm at an excitation wavelength of 490-510 nm, preferably 492-508 nm, preferably 495-505 nm, preferably 497-504 nm, preferably 500-503 nm, or about 502 nm. In one embodiment, this "green" fluorescence (wavelength ~495-570 nm) may be ascribed to the electron transfer from the unsubstituted nitrogen of the imidazole moiety in the compound of formula (I) to the fluorescein ring and/or xanthene moiety of the compound of formula (I). This long wavelength of excitation (502 nm) and emission (525 nm) can prevent interference by autofluorescence from native cellular species, damage to living biological samples, and the influence of background fluorescence.

As used herein, quantum yield (Φ) refers to the fluorescence quantum yield and gives the efficiency of the fluorescence process. It is defined as the ratio of the number of photons emitted to the number of photons absorbed. The maximum fluorescence quantum yield is 1.0 (100%); wherein each photon absorbed results in a photon emitted. Compounds with quantum yields of 0.10 are still considered quite fluorescent. An alternative way to define the quantum yield of fluorescence is by the rate of excited state decay. In a preferred embodiment, the fluorescent Schiff base of formula (I) has a fluorescence with an emission peak centered at 515-535 nm at an excitation wavelength of 490-510 nm with a quantum yield in the range of 0.2-0.8, preferably 0.22-0.7, preferably 0.25-0.5, preferably 0.28-0.4, preferably 0.3-0.35.

As used herein, and throughout coordination chemistry, a ligand refers to an ion or molecule that binds to a central metal atom to form a coordination complex. The binding between metal and ligand generally involves formal donation of one or more of the ligand's electron pairs. The nature of the metal-ligand bonding can range from covalent to ionic. Furthermore, the metal-ligand bond order can range from one to three. Ligands are commonly viewed as Lewis bases. Chelation describes a particular way that molecules bind metal ions, and involves the formation or presence of two or more separate coordinate bonds between a polydentate (multiple bonded) ligand and a single central atom. Often, these ligands are organic compounds and may be referred to as chelants, chelators, chelating agents, or sequestering agents. The chelate effect describes the enhanced affinity of chelating ligands for a metal ion compared to the affinity of a collection of similar non-chelating (i.e. monodentate) ligands for the same metal.

In terms of the present disclosure, the fluorescent Schiff base of formula (I) in any of its embodiments, binds with one or more $Cu^{2+}$ ions by monodentate coordination, bidentate chelation or tridentate chelation to the $Cu^{2+}$ ion to form a metal ion complex. Although transition metals do not differ relatively that much in size, they can establish coordinative interactions at very different energies, which often time can be used for discriminative purposes or selective properties in binding. This phenomenon is consistent with copper, which occurs highest on the Irving-Williams series. The Irving-Williams series refers to the relative stabilities of complexes fobbed by transition metals and the observation that the stability of complexes formed by divalent first-row transition metal ions generally increase across the period to a maximum stability at copper: $Mn(II) < Fe(II) < Co(II) < Ni(II) < Cu(II) > Zn(II)$. This stability is generally explained by factors including, but not limited to, ionic radius, the crystal field stabilization energy and/or the Jahn-Teller effect. In a preferred embodiment, the fluorescent Schiff base of formula (I) forms a metal ion complex with the $Cu^{2+}$ ion which possesses a high thermodynamic affinity for the imino nitrogen, the amide carbonyl group and the imidazole nitrogen functionalities present in the fluorescent Schiff base of formula (I). In certain embodiments, these fast metal-to-ligand binding kinetics may not be possible with other transition metal ions. In certain embodiments, the presence of the alkyl group of the imidazole may be structurally important for the binding of $Cu^{2+}$ ions by i) forcing a conformation that enhances copper coordination in a polydentate manner or ii) by increasing the electron density around the imidazole nitrogen. In certain embodiments, these functionalities serve as high selectivity and high affinity receptors and/or ligands for $Cu^{2+}$ ions.

In certain embodiments, it is equally envisaged that the fluorescent Schiff base of the present disclosure may be adapted or chemically modified to incorporate and/or bind additional metal ions. In some embodiments, these additional metal ions may be used in addition to, or in lieu of $Cu^{2+}$ and may bind selectively or collectively. In one embodiment, the additional metal ion may be any ion which is suitably coordinated by the fluorescent Schiff base compounds of formula (I) in any of their embodiments. Exemplary additional metal ions include, but are not limited to, an alkali metal (Li, Na, K, etc.), an alkaline earth metal (Mg, Ca, Sr, etc.) a lanthanide metal (La, Ce, Eu, Yb, etc.), an actinide metal (Ac, Th, etc.), or a post-transition metal (Al, Sn, Pb, In, etc.). Preferably the additional metal ion is a transition metal ion. Exemplary additional transition metals of the metal ion include, but are not limited to, Sc, Ti, Cr, Mn, Fe, Co, Ni, Cu, Zn, Y, Zr, Pd, Ag, Cd, W, Os, Au, and Hg. Further, the additional metal ion may be of any oxidation state, $M^{+1}$, $M^{+2}$, $M^{+3}$, etc. Preferably, the additional metal ion is at least one selected from the group consisting of $Ag^{2+}$, $Pb^{2+}$, $Ca^{2+}$, $Ni^{2+}$, $Co^{2+}$, $K^+$, $Zn^{2+}$, $Al^{3+}$, $Fe^{3+}$, $Fe^{2+}$, $Na^+$, $Mg^{2+}$, $Hg^{2+}$, $Rb^+$, and $Cs^+$.

In a preferred embodiment, upon binding and/or contacting with one or more $Cu^{2+}$ ions the ultraviolet visible absorption of the fluorescent Schiff base of formula (I) in any of its embodiments with an absorption peak centered at 330-350 nm, preferably 335-348 nm, preferably 338-346 nm, preferably 340-344 nm, or about 342 nm decreases in intensity synchronously to a new redshifted and increasing ultraviolet visible absorption with an absorption peak centered at 490-510 nm, preferably 492-508 nm, preferably 495-505 nm, preferably 497-504 nm, preferably 500-503 nm, or about 502 nm. In certain embodiments, this binding and/or contacting may be accompanied by a color change from colorless to light yellow. In one embodiment, this absorption band centered at 490-510 nm may be attributed to the ring opening of the spirolactam of the fluorescent Schiff base of formula (I) triggered due to the binding of the $Cu^{2+}$ ion.

As used herein, an isosbestic point refers to in spectroscopy a specific wavelength, wavenumber or frequency at which the total absorbance of a sample does not change during a chemical reaction or a physical change of the sample. In a preferred embodiment, the ultraviolet visible absorption of the fluorescent Schiff base of formula (I) in any of its embodiments has an isosbestic point during the addition and binding of one or more $Cu^{2+}$ ions to form a metal ion complex of 350-390 nm, preferably 355-385 nm, preferably 360-380 nm, preferably 365-375 nm, preferably 368-373 nm, or about 372 nm. In a preferred embodiment, the absorption band centered at 490-510 nm linearly increased, respectively, up to 1.0 equivalents of $Cu^{2+}$ indicating the formation of a 1:1 complex with a strong binding affinity that can be confirmed by a Job's plot used to determine the stoichiometry of a binding event. In a preferred embodiment, this response is selective for only $Cu^{2+}$ under these conditions and the addition of up to 25 equivalents, preferably up to 20, preferably up to 15, preferably up to 10, preferably up to 5 equivalents of other common metal ions including, but not limited to, alkalis, alkaline earths, and transition metals produce minimal or no appreciable ultraviolet visible absorption spectral changes.

In a preferred embodiment, upon binding and/or contacting with one or more $Cu^{2+}$ ions the fluorescence of the fluorescent Schiff base of formula (I) in any of its embodiments with an emission peak centered at 515-535 nm, preferably 518-532 nm, preferably 520-530 nm, preferably 522-528 nm, or about 525 nm at an excitation wavelength of 490-510 nm, preferably 492-508 nm, preferably 495-505 nm, preferably 497-504 nm, preferably 500-503 nm, or about 502 nm is quenched and/or inhibited. As used herein, "quenching" refers to any process which decreases the fluorescence intensity of a given substance. A variety of processes can result in quenching including, but not limited to, excited state reactions, energy transfer, complex formation and collisional quenching. In certain embodiments, this binding and/or contacting may be accompanied by a complete quenching of the "green" fluorescence upon illumination at 300-400 nm, preferably 320-390 nm, preferably 340-380 nm, preferably 350-375 nm, preferably 360-370 nm, or about 365 nm. As $Cu^{2+}$ is a paramagnetic cation, with open shell d-orbitals, the quenching of the fluorescence upon binding with it may be attributed to inhibition of the electron transfer from the imidazole of the fluorescein and/or xanthene moiety providing a very fast and efficient non-radiative decay of the excited state.

In a preferred embodiment, the fluorescent Schiff base of formula (I) upon excitation at a wavelength of 490-510 nm gave a strong fluorescence emission peak at 515-535 nm and that emission is completely quenched upon the addition of $Cu^{2+}$. In a preferred embodiment, the fluorescence emission centered at 515-535 nm showed a linear diminution with an increase $Cu^{2+}$ concentration when the ratio of $Cu^{2+}$ to the fluorescent Schiff base of formula (I) is less than or equal to 1:1 and once the 1:1 ratio is reached higher $Cu^{2+}$ concentrations do not lead to any further emission effects. In a preferred embodiment, this response is selective for only $Cu^{2+}$ under these conditions and the addition of up to 25 equivalents, preferably up to 20, preferably up to 15, preferably up to 10, preferably up to 5 equivalents of other common metal ions including, but not limited to, alkalis, alkaline earths, and transition metals produce minimal or no appreciable fluorescence emission spectral changes including no distinct emission shift or quenching. Further competitive binding experiments with different metal ions are capable of demonstrating that additional metal ions do not interfere with the quenching of the fluorescent Schiff base of formula (I) by $Cu^{2+}$.

As used herein, the binding constant is a special case of the equilibrium constant (K of $K_a$). It is associated with the binding and unbinding reaction of receptor and ligand molecules. The reaction is characterized by the on-rate constant and the off-rate constant. In equilibrium, the forward binding transition should be balanced by the backward unbinding transition. The binding constant or association constant is defined by the on-rate constant divided by the off-rate constant or the concentration receptor-ligand complexes (i.e. metal ion complexes) divided by the concentration of unbound free receptors and divided by the concentration of unbound free ligand. In certain embodiments, the binding of copper with the fluorescent Schiff base of formula (I) follows a 1:1 stoichiometric complex formation as can be confirmed by fluorescence titration, the Job's plot and the HR-mass of the metal ion complex, thus the quenching by $Cu^{2+}$ can be assumed to occur in a static quenching mode due to the formation of a non-fluorescent complex in the ground state and the linear Stern-Volmer plot can be used to calculate a binding constant. In a preferred embodiment, the fluorescent Schiff base of formula (I) in any of its embodiments has a $Cu^{2+}$ binding constant in the range of $0.5 \times 10^7$ $L \cdot mol^{-1}$ to $1.5 \times 10^7$ $L \cdot mol^{-1}$ as calculated from fluorescence titration, preferably $0.6 \times 10^7$ $L \cdot mol^{-1}$ to $1.4 \times 10^7$ $L \cdot mol^{-1}$, preferably $0.7 \times 10^7$ $L \cdot mol^{-1}$ to $1.3 \times 10^7$ $L \cdot mol^{-1}$, preferably $0.8 \times 10^7$ $L \cdot mol^{-1}$ to $1.2 \times 10^7$ $L \cdot mol^{-1}$, $0.9 \times 10^7$ $L \cdot mol^{-1}$ to $1.1 \times 10^7$ $L \cdot mol^{-1}$, preferably $0.95 \times 10^7$ $L \cdot mol^{-1}$ to $1.05 \times 10^7$ $L \cdot mol^{-1}$, or about $1.0 \times 10^7$ $L \cdot mol^{-1}$ as calculated from fluorescence titration. In other embodiments, absorption and/or emission titration and a variety of methods may be used to calculate a binding constant.

According to a second aspect, the present disclosure relates to a process for producing the fluorescent Schiff base of formula (I) in any of its embodiments comprising i) refluxing a fluorescein or rhodamine based compound with hydrazine to form a fluorescein or rhodamine based hydrazide and ii) refluxing the fluorescein or rhodamine based hydrazide with a N-alkylimidazole-2-carboxaldehyde to form the fluorescent Schiff base of formula (I) of the present disclosure.

In one step of the process, a fluorescein or rhodamine based compound is refluxed with hydrazine to form a fluorescein or rhodamine based hydrazide. In a preferred embodiment, the fluorescein or rhodamine based compound is a compound of formula (II)

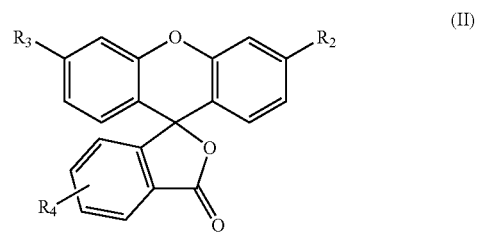

or a salt, solvate, tautomer or stereoisomer thereof, wherein i) $R_2$ and $R_3$ are independently —OH, —$NH_2$, —$OR_5$, —$NHR_5$, —$NR_5R_5$, preferably $R_2$ and $R_3$ are —OH or —$NH2$ ii) $R_4$ is —H, —F, —Cl, —Br, —CN, —OH, —$OR_5$, —$NO_2$, —$NH_2$, —$NHR_5$, —$NR_5R_5$, and each $R_5$ is independently an optionally substituted alkyl, optionally substituted cycloalkyl, or optionally substituted aryl, preferably $R_4$ is —H. In a preferred embodiment, the compound of formula (II) is fluorescein, compound 4

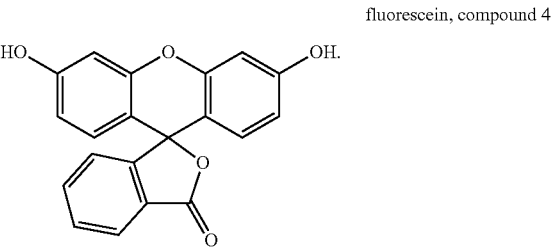 [SMILES: O=C1OC2(c3ccc(O)cc3Oc3cc(O)ccc32)c2ccccc21]

In a preferred embodiment, the fluorescein or rhodamine based hydrazide is a compound of formula (III)

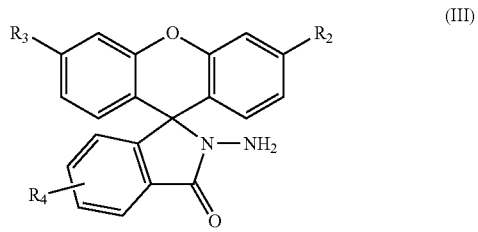

or a salt, solvate, tautomer or stereoisomer thereof, wherein i) $R_2$ and $R_3$ are independently —OH, —$NH_2$, —$OR_5$, —$NHR_5$, —$NR_5R_5$, preferably $R_2$ and $R_3$ are —OH or —$NH2$ ii) $R_4$ is —H, —F, —Cl, —Br, —CN, —OH, —$OR_5$, —$NO_2$, —$NH_2$, —$NHR_5$, —$NR_5R_5$, and each $R_5$ is independently an optionally substituted alkyl, optionally substituted cycloalkyl, or optionally substituted aryl, preferably $R_4$ is —H. In a preferred embodiment, the compound of formula (III) is

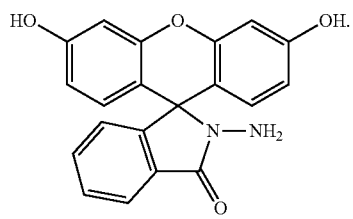

compound 2

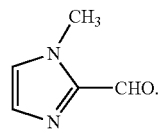

compound 3

In a preferred embodiment, the refluxing is performed in a polar protic solvent, preferably methanol. Exemplary additional polar protic solvents that may be used in addition to or in lieu of methanol, include but are not limited to formic acid, n-butanol, isopropanol, n-propanol, ethanol, acetic acid and water. It is equally envisaged that the refluxing may be adapted to be performed in a polar aprotic solvent (i.e. tetrahydrofuran, ethyl acetate, acetone, dimethylformamide, acetonitrile, dimethyl sulfoxide, nitromethane and propylene carbonate) or a non-polar solvent (i.e. pentane, cyclopentane, hexane, cyclohexane, benzene, toluene, 1,4-dioxane, chloroform, diethyl ether and dichloromethane). In a preferred embodiment the hydrazine is present in the reaction in a molar excess to the fluorescein or rhodamine based compound in the range of 1.1 to 2 equivalents, preferably, 1.15-1.5 equivalents, or about 1.2 equivalents. In a preferred embodiment, the refluxing is performed in a closed flask with mechanical stirring at a temperature of up to 110° C., preferably 20-100° C., preferably 40-80° C., preferably 50-75° C., preferably 55-70° C. and has a stirred reaction time of up to 24 hr, preferably 2-24 hr, preferably 4-20 hr, preferably 8-16 hr, preferably 10-12 hr. In a preferred embodiment, this reaction results in a precipitate that may be separated (filtered), washed and dried to give a solid, preferably yellow in color, and has a yield of greater than 60%, preferably greater than 70%, preferably greater than 75%, preferably greater than 80%, preferably greater than 83%, preferably greater than 85%.

In one step of the process, the fluorescein or rhodamine based hydrazide compound is refluxed with a N-alkylimidazole-2-carboxaldehyde to form the fluorescent Schiff base of formula (I). The synthesis and preparation of N-alkylimidazole-2-carboxaldehyde compounds is well known in the literature and to those of ordinary skill in the art. In a preferred embodiment, the N-alkylimidazole-2-carboxaldehyde is a compound of formula (IV)

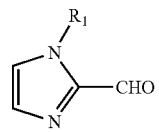

(IV)

or a salt, solvate, tautomer or stereoisomer thereof, wherein $R_1$ is an optionally substituted alkyl, optionally substituted cycloalkyl, or optionally substituted aryl, preferably $R_1$ is $-CH_3$ or $-CH_2CH_3$. In a preferred embodiment, the compound of formula (IV) is In a preferred embodiment, the refluxing is performed in a polar protic solvent, preferably ethanol. Exemplary additional polar protic solvents that may be used in addition to or in lieu of ethanol, include but are not limited to formic acid, n-butanol, isopropanol, n-propanol, methanol, acetic acid and water. It is equally envisaged that the refluxing may be adapted to be performed in a polar aprotic solvent (i.e. tetrahydrofuran, ethyl acetate, acetone, dimethylformamide, acetonitrile, dimethyl sulfoxide, nitromethane and propylene carbonate) or a non-polar solvent (i.e. pentane, cyclopentane, hexane, cyclohexane, benzene, toluene, 1,4-dioxane, chloroform, diethyl ether and dichloromethane). In some embodiments, a catalytic amount of acetic acid may also be employed. In a preferred embodiment the N-alkylimidazole-2-carboxaldehyde is present in the reaction in a molar excess to the fluorescein or rhodamine based hydrazide in the range of 1.1 to 2 equivalents, preferably, 1.15-1.5 equivalents, or about 1.2 equivalents. In a preferred embodiment, the refluxing is performed in a closed flask with mechanical stirring at a temperature of up to 110° C., preferably 20-100° C., preferably 40-80° C., preferably 60-78° C., preferably 65-75° C. and has a stirred reaction time of up to 24 hr, preferably 2-24 hr, preferably 4-20 hr, preferably 8-16 hr, preferably 10-12 hr. In a preferred embodiment, this reaction results in a precipitate that may be separated (filtered), washed and dried to give a solid, preferably yellow in color, and has a yield of greater than 60%, preferably greater than 70%, preferably greater than 75%, preferably greater than 80%, preferably greater than 83%, preferably greater than 85%.

According to a third aspect, the present disclosure relates to a method for detecting and quantifying $Cu^{2+}$ ions in a fluid sample comprising i) contacting the fluid sample with the fluorescent Schiff base of formula (I) in any of its embodiments and ii) measuring the fluorescence emission at 515-535 nm with an excitation wavelength of 490-510 nm to determine a concentration of $Cu^{2+}$ ions in the fluid sample, wherein during the contacting the fluorescent Schiff base binds to the $Cu^{2+}$ ions at a molar ratio of 1:1 and quenches and/or inhibits the fluorescence emission.

In terms of the present disclosure, the fluid sample may be an inorganic sample including aqueous solutions, water sources and systems. Non-limiting examples of aqueous solutions (i.e. $Cu^{2+}$ contaminated aqueous solutions), water sources and systems include, but are not limited to surface water that collects on the ground or in a stream, aquifer, river, lake, reservoir or ocean, ground water that is obtained by drilling wells, run-off, industrial water, industrial effluent water, tap water, public water storage towers, public recreational pools and/or bottled water. In other embodiments, the fluid sample may be a biological sample including, but not limited to urine, whole blood, dried blood and blood plasma. It is further envisaged that the method of the present disclosure may be used for detecting and quantifying metal ions (i.e. $Cu^{2+}$ ions) in applications including, but not limited to, water quality monitoring, pollution control, pharmaceutical and cosmetics industry quality control, food quality control, agriculture and fishery industries, medical diagnosis, industrial waste production, waste water treatment, and as a research tool. The method and compounds of the present disclosure may advantageously be used for detecting and quantifying heavy metal ions (i.e. $Cu^{2+}$ ions) that are of environmental or human health concerns. In a preferred embodiment, the fluid sample is at least one selected from the group consisting of contaminated water, a consumable good, and a bodily fluid.

In a preferred embodiment, the fluid sample is an aqueous sample comprising greater than 10% v/v of water, preferably 10-99% v/v, preferably 20-80% v/v, preferably 30-75% v/v of water. In certain embodiments, the fluid sample may further comprise up to 90% v/v of an organic solvent, such as the polar protic short chain alcohols including, but not limited, methanol, ethanol, n-propanol, isopropanol, n-butanol and mixtures thereof as secondary solvents, preferably methanol. In a preferred embodiment, the fluid sample may comprise 5-90% v/v of methanol, preferably 10-60% v/v, preferably 15-40% v/v, preferably 20-30% v/v of methanol. In one embodiment, the fluid sample may comprise 20% v/v of methanol and 80% v/v of water.

As used herein, a buffer solution (more precisely, pH buffer or hydrogen ion buffer) refers to an aqueous solution consisting of a mixture of a weak acid and its conjugate base, or vice versa. Its pH changes very little when a small or moderate amount of strong acid or base is added to it and thus it is used to prevent changes in the pH of a solution. Buffer solutions are used as a means of keeping pH at a nearly constant value in a wide variety of chemical applications. In certain embodiments, the fluid sample further comprises a buffer solution, preferably HEPES buffer. Additional exemplary appropriate buffers include, but are not limited to TAPS, Bicine, Glycylglycine, Tris, HEPPSO, EPPS, HEPPS, POPSO, N-ethylmorpholine, TEA (Triethanolamine), Tricine, TAPSO, DIPSO, TES, BES, phosphoric acid, MOPS, imidazole PIPES and the like. In a preferred embodiment, the fluid sample has a pH in the range of 4.5-10.5, preferably 5-10, preferably 6-9.5, preferably 6.5-8, preferably 6.8-7.8, preferably 7-7.6 or about 7.4. For environmental and physiological applications of the fluorescent Schiff base compounds of formula (I), especially as chemosensors, the sensing should operate in a wide range ideally showing no physiological pH sensitivity. In a preferred embodiment, the fluorescent Schiff based compounds of formula (I) exist as a closed spirocyclic form at neutral and basic pH, decreasing pH (<4.5) protonates the nitrogen of the imidazole ring and thus inhibits the electron transfer thus decreasing the fluorescence and a higher pH (>10.5) fluorescence intensity is decreased by an enhancement of negative charge density on the imidazole ring and possible formation of a phenolate on the xanthene moiety.

In terms of the present disclosure, the method and contacting may be carried out in tanks, containers, or small scale applications in both batch mode and/or fixed-bed or column mode. In an exemplary batch mode, the fluorescent Schiff base compound of formula (I) is added and dispersed into a fluid sample at a concentration of 0.1-100 µM, preferably 1-50 µm, preferably 2-40 µM, preferably 5-25 µM, preferably 5-15 µM and is present at a concentration of 0.1-25 µM during the measuring, preferably 0.5-15 µM, preferably 1-10 µM, preferably 2-5 µM during the measuring. In one embodiment, the fluorescent Schiff base compound of formula (I) is present at a concentration of 0.2 µM during the measuring. In another embodiment, the fluorescent Schiff base compound of formula (I) is present at a concentration of 20.0 µM during the measuring. During the contacting, the fluorescent Schiff base of the present disclosure preferably forms a metal ion complex having a 1:1 binding mode with $Cu^{2+}$ ions. The fluorescence signal emission peak centered at 515-535 nm, preferably 518-532 nm, preferably 520-530 nm, preferably 522-528 nm, or about 525 nm at an excitation wavelength of 490-510 nm, preferably 492-508 nm, preferably 495-505 nm, preferably 497-504 nm, preferably 500-503 nm, or about 502 nm is then measured spectrophotometrically and the presence of $Cu^{2+}$ is manifested as a quench or reduction or inhibition of this fluorescent emission. In certain embodiments, the binding of the fluorescent Schiff base of formula (I), preferably the 1:1 binding, further results in an ultraviolet visible absorption with an absorption peak centered at 490-510 nm, preferably 492-508 nm, preferably 495-505 nm, preferably 497-504 nm, preferably 500-503 nm, or about 502 nm that is substantially not present in the fluid sample prior to the contacting. Thus, the fluorescent Schiff base compounds of formula (I) described herein can be considered a "turn-off" fluorescent sensor or chemosensor in both absorption and emission modes.

In the fixed mode, the fluorescent Schiff base compound of formula is affixed to a substrate (i.e. a plate or a column) which is then immersed in a fluid sample, preferably in the concentration ranges previously described. In one or more embodiments, the $Cu^{2+}$ detection and quantification method described herein may further comprise and/or be preceded by calibration procedures with steps including measuring the fluorescence emission of a plurality of calibration fluid samples comprising a series of known amounts of $Cu^{2+}$ in the same medium as the fluid sample to be tested, in order to obtain a calibration curve.

In a preferred embodiment, the method of detecting and quantifying described herein has a $Cu^{2+}$ detection lower limit of 0.01-0.05 µM in the fluid sample without interference from one or more additional metal ions, preferably 0.015-0.045 µM, preferably 0.02-0.042 µM, preferably 0.025-0.04 µM, preferably 0.034-0.038 µM or about 0.037 µM in the fluid sample without interference from one or more additional metal ions. In a preferred embodiment, the one or more additional metal ions are selected from the group consisting of $Ag^{2+}$, $Pb^{2+}$, $Ca^{2+}$, $Ni^{2+}$, $Co^{2+}$, $K^+$, $Zn^{2+}$, $Al^{3+}$, $Fe^{3+}$, $Fe^{2+}$, $Na^+$, $Cd^{2+}$, $Mg^{2+}$, $Hg^{2+}$, $Rb^+$, and $Cs^+$. In certain embodiments, these additional metal ions may be present in up to 50 equivalents excess to the fluorescent Schiff base compound of formula (I) without interference, preferably up to 40 equivalents, preferably up to 30 equivalents, preferably up to 20 equivalents, preferably up to 10 equivalents excess to the fluorescent Schiff base compound of formula (I) without interference.

In certain embodiments, it is equally envisaged that the method of the present disclosure may be adapted to incorporate a chemically modified fluorescent Schiff base designed to bind and therefore detect and quantify additional metal ions. In some embodiments, these additional metal ions may be detected and quantified in addition to, or in lieu of $Cu^{2+}$ and may bind selectively or collectively. In one embodiment, the additional metal ion may be any ion which is suitably coordinated by the fluorescent Schiff base compounds of formula (I) in any of their embodiments. Exemplary additional metal ions include, but are not limited to, an alkali metal (Li, Na, K, etc.), an alkaline earth metal (Mg, Ca, Sr, etc.) a lanthanide metal (La, Ce, Eu, Yb, etc.), an actinide metal (Ac, Th, etc.), or a post-transition metal (Al, Sn, Pb, In, etc.). Preferably the additional metal ion is a transition metal ion. Exemplary additional transition metals of the metal ion include, but are not limited to, Sc, Ti, Cr, Mn, Fe, Co, Ni, Cu, Zn, Y, Zr, Pd, Ag, Cd, W, Os, Au, and Hg. Further, the additional metal ion may be of any oxidation state, $M^{+1}$, $M^{+2}$, $M^{+3}$, etc. Preferably, the additional metal ion is at least one selected from the group consisting of $Ag^{2+}$, $Pb^{2+}$, $Ca^{2+}$, $Ni^{2+}$, $Co^{2+}$, $K^+$, $Zn^{2+}$, $Al^{3+}$, $Fe^{3+}$, $Fe^{2+}$, $Na^+$, $Cd^{2+}$, $Mg^{2+}$, $Hg^{2+}$, $Rb^+$, and $Cs^+$.

In a preferred embodiment, the binding of the fluorescent Schiff base of formula (I) to the $Cu^{2+}$ ions is a chemically reversible process and the introduction of a chelator restores the fluorescence emission centered at 515-535 nm. In certain embodiments, the introduction of a chelator including, but not limited to, natural chelators (tetrapyrrols, ferrioxamines, phenolics, ionophores such as gramicidin, monoensin, valinomycin), synthetic chelators (2,2'-bipyridyl, dimercaptopropanol, salicylic acid, triethanolamine, ionophores such as nitrilotriacetic acid and heavy metal chelators (EDTA, DMPS, DMSA, etc.) to a sample containing the metal ion complexed solution causes the fluorescence of the sample to be instantly recovered. In this manner the fluorescent Schiff base of formula (I) may be regenerated and reused and substrates (i.e. plates and columns) may be cleaned and reused. In certain embodiments, this may be accompanied by a color change to colorless from light yellow. In a preferred embodiment, the chelator may be added to the complexed solution at a concentration of 0.01-5.0 µM, preferably 0.5-4.0 µM, preferably 1.0-3.0 µM or about 2.0 µM and alternatively may be present in up to 50 equivalents excess to the fluorescent Schiff base compound of formula (I), preferably up to 40 equivalents, preferably up to 30 equivalents, preferably up to 20 equivalents, preferably up to 10 equivalents excess to the fluorescent Schiff base compound of formula (I). In a preferred embodiment, the chelator is a heavy metal chelator selected from the exemplary list including, but not limited to, ethylenediaminotetraacetic acid (EDTA), 2,3-dimercaptopropanesulfonic acid (DMPS), dimercaptosuccinic acid (DMSA), dimercaptopropanol, penicillamine, ethylenediamine tetraacetic acid calcium disodium versante ($CaNa_2$-EDTA), dimercaprol, deferoxamine, deferasirox, EGTA, ethylenedioxy-diethylene-dinitrilo-tetraacetic acid and the like, most preferably the chelator is EDTA.

In one embodiment, the method further comprises washing the heavy metal loaded fluorescent Schiff base metal ion complex free of the heavy metal ions to reform the fluorescent Schiff base such that the fluorescent Schiff base can be recycled and/or reused in another contacting, detecting, and/or quantifying. In a preferred embodiment, the fluorescent Schiff base can be reused up to 15 times without a loss in detection limit or capacity, preferably up to 12 times, preferably up to 10 times, preferably up to 8 times, more preferably up to 5 times.

Further to measurements relating to electric potential, absorbance, and fluorescence the fluorescent Schiff base compounds of formula (I) may be used to detect transition metal ions, such as $Cu^{2+}$, using other known spectroscopic techniques. Further, the method may be used to detect metal ions in redox processes, and the spectroscopic method may depend on a redox reaction. The ion pair complexing method and the redox method may further depend on color changes as a result of the metal ion complex formed between a transition metal ion and the fluorescent Schiff base compounds. In another embodiment, after the metal ions in a sample solution are detected and/or quantified according to the methods described in the present disclosure, it is envisioned that various methods and techniques may be implemented to separate and remove the metal ions from solutions. Such methods and techniques are known to those of ordinary skill in the art. In some embodiments, the binding of the metal ions to the fluorescent Schiff base compounds may result in aggregation and aid in this removal of the metal ions.

The examples below are intended to further illustrate methods protocols for preparing and characterizing the fluorescent Schiff base compounds of the present disclosure. Further, they are intended to illustrate assessing the properties of these compounds. They are not intended to limit the scope of the claims.

Example 1

General Methods and Characterization of Prepared Compounds

Melting points were determined using a Thomas-Hoover capillary melting point apparatus and are uncorrected. $^1H$ and $^{13}C$ NMR spectra were recorded on a Bruker AM-400 spectrometer using $Me_4Si$ as the internal standard. UV-vis absorption spectra were determined on a Jasco V-670 spectrophotometer equipped with a xenon discharge lamp and 1 cm quartz cells. All of the measurements were carried out at 298 K.

Analytical grade absolute ethanol and methanol were purchased from Merck. Deionized water (double distilled) was used throughout the experiments as an aqueous layer. All other materials used for synthesis were purchased from Aldrich Chemical Co. and used as received without further purification. The N-methylimidazole-2-carbaldehyde (Compound 3) was prepared in accordance with literature procedures [Fasil, A.; Abebe, C.; Eribal, S.; Ramakrishna, G.; Sinn, E. *Tetrahedron Lett.* 2011, 52 5554.; and Sivaraman, G.; Chellappa, D. *J Mater. Chem.* B 2013, 1, 5768.; and Ding, J.; Yuan, L.; Gao, L.; Chen, J. *J. Lumin.* 2012, 132, 1987.; and Sivaraman, G.; Sathiyaraja, V.; Chellappa, D. *J. Lumin.* 2014, 145, 480.—each incorporated herein by reference in its entirety]. The solutions of metal ions were prepared from their nitrate and chloride salts of analytical grade, and then subsequently diluted to prepare working solutions. HEPES buffer solutions of different pH were prepared using proper amounts of HEPES and KOH (all of analytical grade) under adjustment by a Mettler Toledo pH meter.

Example 2

Synthesis of fluorescein-N-methylimidazole Conjugate (Compound 1)

Fluorescein-N-methylimidazole conjugate compound 1 was designed to bind metal ions via the carbonyl oxygen, imino nitrogen groups and the imidazole nitrogen atoms as donors. FIG. 1 outlines the primary scheme for the syntheses of compound 1 from the reaction of fluorescein hydrazide compound 2 with N-methylimidazole-2-carbaldehyde compound 3 in ethanol. The synthesis of fluorescein hydrazide compound 2 was carried out by reacting fluorescein compound 4 with hydrazine ($NH_2NH_2$) in methanol under reflux conditions. The synthesis of N-methylimidazole-2-carbaldehyde compound 3 was carried out according to procedures reported in the literature [Fasil, A.; Abebe, C.; Eribal, S.; Ramakrishna, G.; Sinn, E. *Tetrahedron Lett.* 2011, 52 5554.; and Sivaraman, G.; Chellappa, D. *J Mater. Chem.* B 2013, 1, 5768.; and Ding, J.; Yuan, L.; Gao, L.; Chen, J. *J Lumin.* 2012, 132, 1987.; and Sivaraman, G.; Sathiyaraja, V.; Chellappa, D. *J. Lumin.* 2014, 145, 480.—each incorporated herein by reference in its entirety]. Both of the compounds were prepared in good yield and their structures were confirmed un $^1$H-NMR, $^{13}$C-NMR, mass spectrometry, and elemental analysis.

Fluorescein hydrazide compound 2 (0.5 g, 1.4 mmol) and N-methylimidazole-2-carbaldehyde compound 3 (0.191 g, 1.7 mmol) were suspended in 10 mL of ethanol. The mixture was refluxed for 12 hours with stirring, resulting in the formation of a yellow precipitate. The precipitate was separated by filtration and washed with ethanol (3×10 mL). After drying, a yellowish solid was obtained in 85% yield. $^1$H NMR (400 MHz, DMSO-$d_6$), δ (ppm): 3.74 (s, 3H), 6.38 (d, 6.8 Hz, 3H), 6.42-6.48 (m, 3H), 6.59 (d, 1.6 Hz, 2H), 6.96 (d, 6.4 Hz, 1H), 7.63 (t, 5.6 Hz, 1H), 7.69 (t, 5.6 Hz, 1H), 7.77 (d, 6.8 Hz, 1H), 8.24 (s, 1H), 9.67 (s, 2H). $^{13}$C NMR (400 MHz, DMSO-$d_6$), δ (ppm): 33.82, 64.94, 102.63, 110.1, 112.29, 122.68, 123.59, 128.14, 128.37, 128.47, 128.5, 128.72, 129.33, 129.76, 132.96, 133.3, 151.75, 152.45, 152.59, 158.36, 158.38, 158.86, 159, 164.37, 165.94. Anal Calcd for 1, $C_{25}H_{18}N_4O_4$: C, 68.49; H, 4.14; N, 12.78. Found: C, 68.38; H, 4.15; N, 12.65; HR-mass Calcd for: $C_{25}H_{18}N_4O_4$ [M+H]$^+$: 439.1406. Found: m/z 439.1405. The formation of imine can be easily identified by the =C—H proton singlet peak at DMSO-$d_6$ 8.24 ppm in compound 1. The hydroxyl protons of the fluorescein appear as a single peak at DMSO-$d_6$ 9.67 ppm in compound 1.

Example 3

Synthesis of fluorescein-N-methylimidazole Conjugate (1) $Cu^{2+}$ Complex

A mixture of fluorescein-N-methylimidazole conjugate compound 1 (100 mg, 0.23 mmol) and $Cu(NO_3)_2 \cdot H_2O$ (62 mg, 0.28 mmol) in methanol was refluxed for 8 hours. The mixture was cooled to room temperature and the precipitated complex was filtered. The filtered cake was washed thoroughly with water, ethanol, and dried under vacuum to provide the complex (95 mg, 82% yield). HR-FAB Mass: calcd for $(C_{25}H_{18}O_4N_4.Cu)$ 501.0624; found: 501.0621.

Example 4

Absorption Studies

All of the absorption and emission studies were carried out in mixed aqueous solutions of water and methanol (4:1) containing HEPES buffer (10 mM, pH 7.4) at a concentration of 20 μM and 0.2 μM respectively. Initial studies on the probe compound 1 exhibited an absorption peak centered at 342 nm, which was ascribed to the absorption of the xanthene moiety; however, there was no observable absorption in the visible region evidencing that the probe compound 1 was persisting as the lactam form in the solution [Yin, W.; Zhu, H.; Wang, R. *Dyes Pigments* 2014, 107, 127.; and Zheng, H.; Zhan, X.-Q.; Biana, Q.-N.; Zhanga, X.-J. *Chem. Commun.*, 2013, 49, 429.—each incorporated herein by reference in its entirety].

Figure 2A:
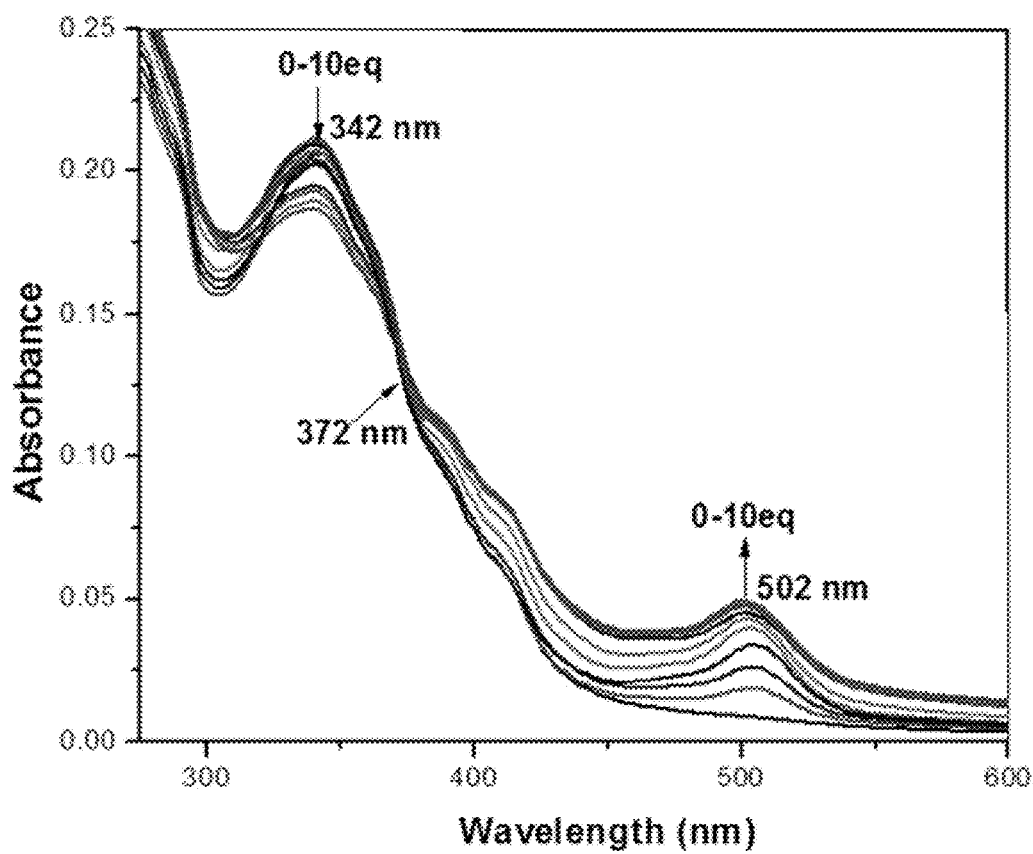
FIG. 2A is an ultraviolet-visible (UV-Vis) spectra of fluorescein-N-methylimidazole conjugate based compound 1 (20 μM) upon the addition of 0-10 molar equivalents of $Cu(NO_3)_2$ in $H_2O$:MeOH (4:1) containing HEPES buffer (10 mM, pH 7.4) solution with saturation occurring after the addition of 1 molar equivalent.
Figure 2B:
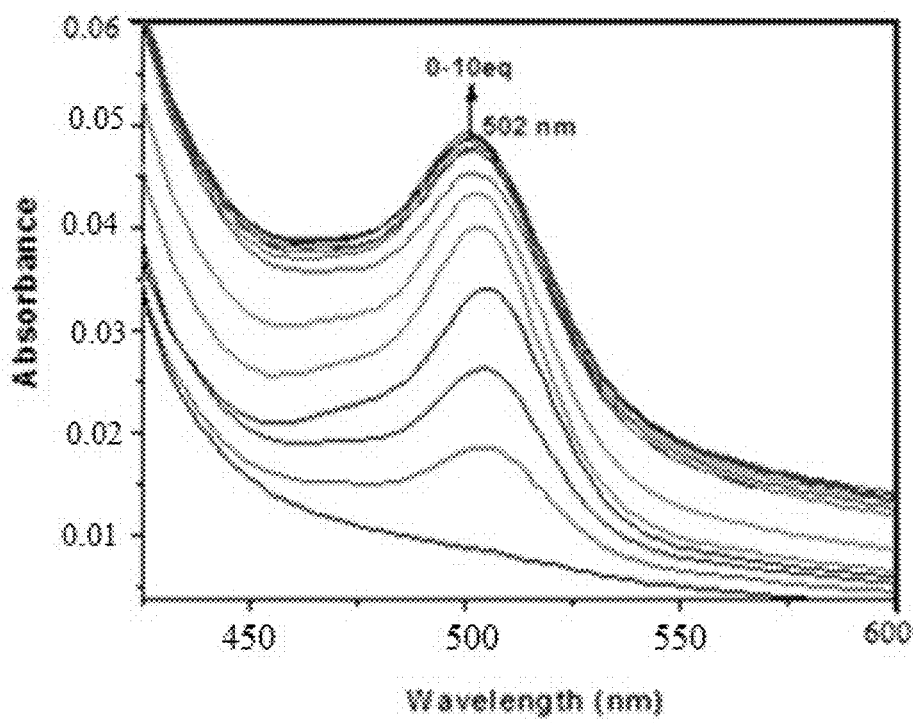
FIG. 2B is an expanded view of an ultraviolet-visible (UV-Vis) spectra of fluorescein-N-methylimidazole conjugate based compound 1 (20 μM) upon the addition of 0-10 molar equivalents of $Cu(NO_3)_2$ in $H_2O$:MeOH (4:1) containing HEPES buffer (10 mM, pH 7.4) solution with saturation occurring after the addition of 1 molar equivalent.
Figure 3:
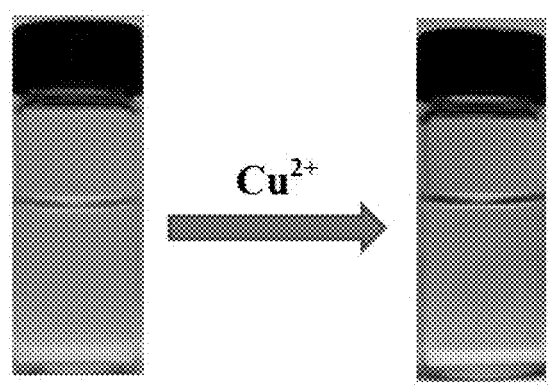
FIG. 3 is a representation of the visible color change from colorless to light yellow of fluorescein-N-methylimidazole conjugate based compound 1 (20 μM) upon the addition of $Cu(NO_3)_2$ in $H_2O$:MeOH (4:1) containing HEPES buffer (10 mM, pH 7.4) solution.
Figure 4:
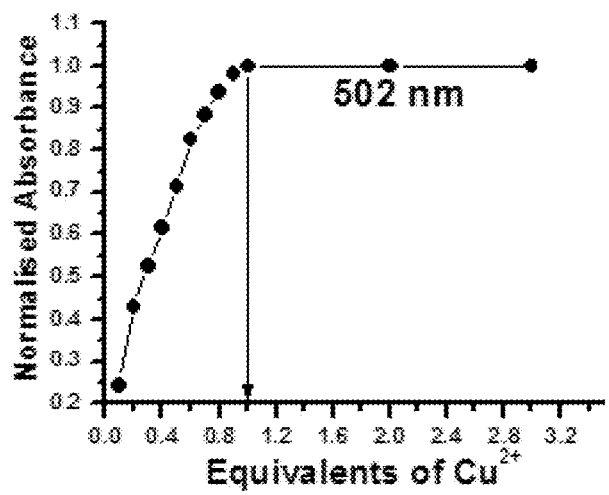
FIG. 4 is a molar ratio plot of normalized absorbance at 502 nm of fluorescein-N-methylimidazole conjugate based compound 1 (20 μM) upon the addition of 0-3 molar equivalents of $Cu(NO_3)_2$ in $H_2O$:MeOH (4:1) containing HEPES buffer (10 mM, pH 7.4) solution.
Figure 5:
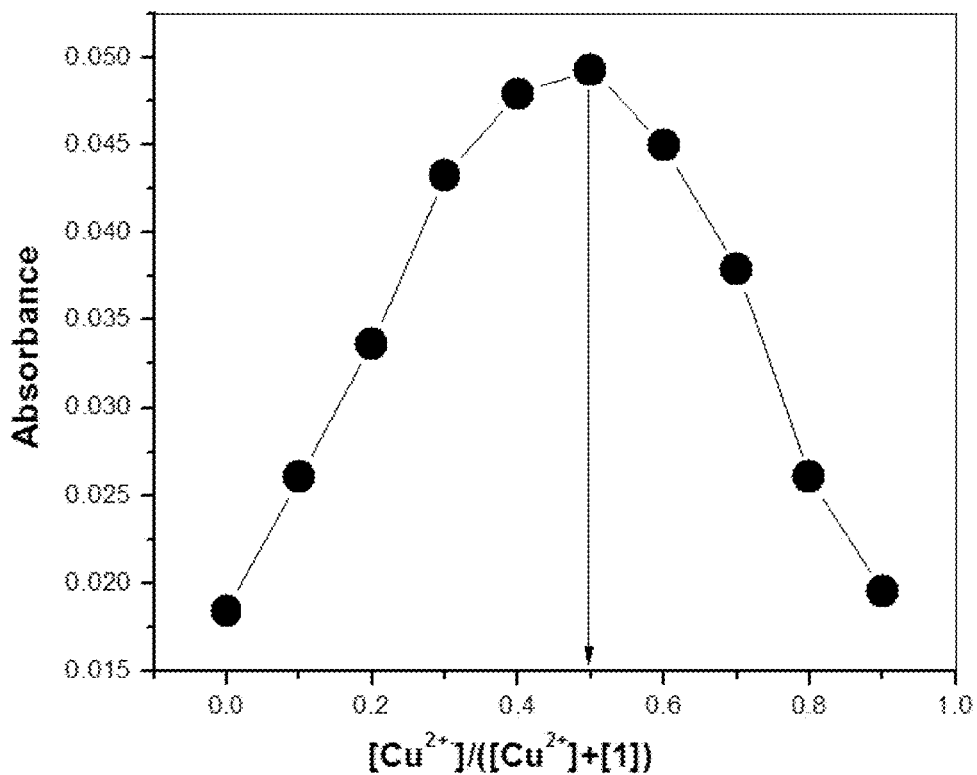
FIG. 5 is a Job's plot of fluorescein-N-methylimidazole conjugate based compound 1 with $Cu^{2+}$.
Figure 6:
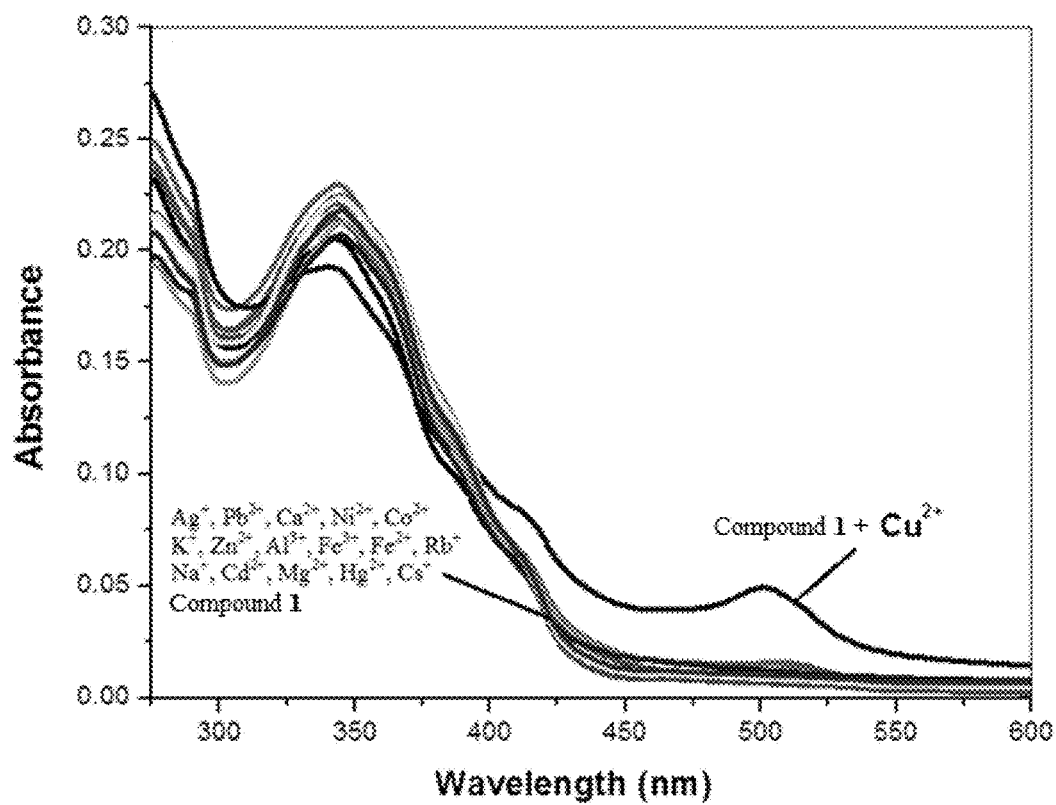
FIG. 6 is a UV-Vis spectra of fluorescein-N-methylimidazole conjugate based compound 1 (20 μM) upon the addition of 10 molar equivalents of different cations in $H_2O$:MeOH (4:1) containing HEPES buffer (10 mM, pH 7.4) solution.

Upon the addition of $Cu^{2+}$ to the solution of compound 1 a new redshifted absorption band at 502 nm is enhanced gradually while the absorption band at 342 nm decreased synchronously, with an isosbestic point at 372 nm as shown in FIG. 2 and evidenced by the color change of the solution from colorless to light yellow (FIG. 3). The peak centered at 502 nm in the UV-vis spectra is attributed to the ring opening of the spirolactam triggered by the binding of $Cu^{2+}$. The respective absorption bands at 502 nm linearly increased up to 1.0 equiv of $Cu^{2+}$ (FIG. 4) indicating the formation of a 1:1 complex with a strong binding affinity. The Job's plot of compound 1 with $Cu^{2+}$ also confirmed the formation of a 1:1 complex (FIG. 5). This response was selective for only $Cu^{2+}$ under these conditions. The additions of 10 equiv of the other common metal cations, particularly the alkalis, alkaline earth, and transition metals produce minimal or no appreciable spectral changes (FIG. 6).

Example 5

Emission Studies

Figure 7:
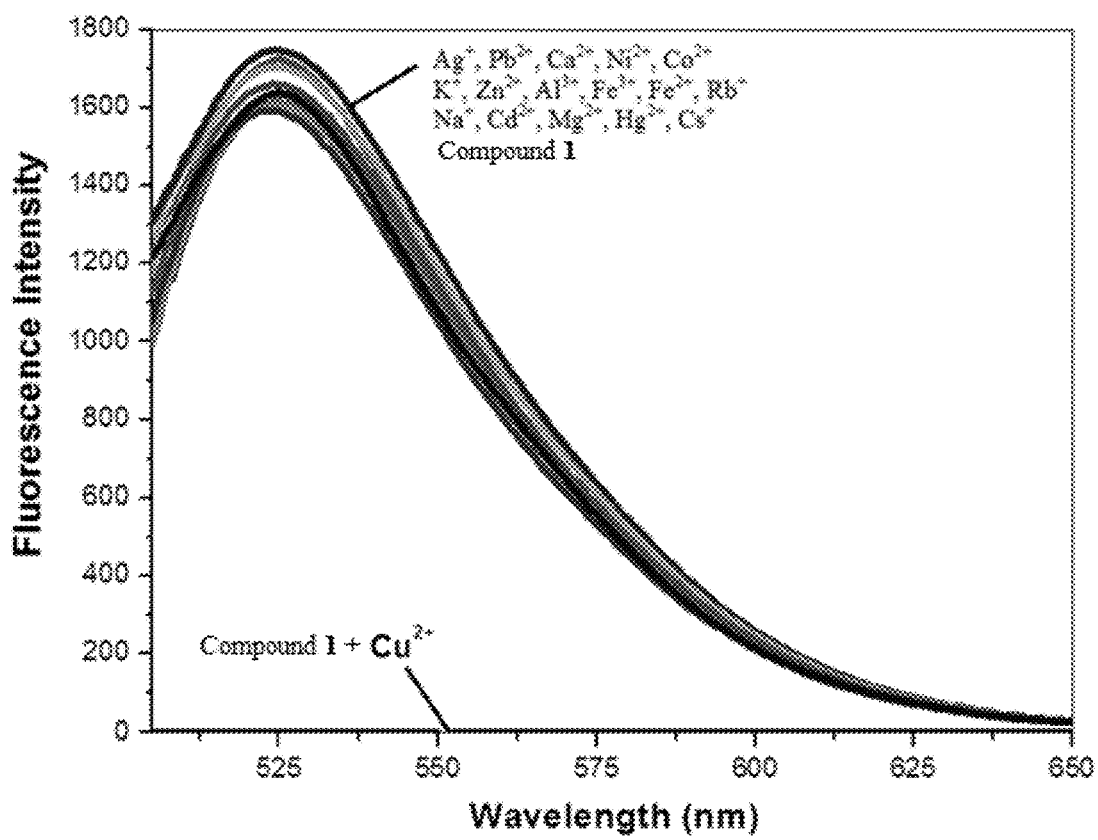
FIG. 7 is a fluorescence spectra of fluorescein-N-methylimidazole conjugate based compound 1 (0.2 μM) upon the addition of 10 molar equivalents of different cations in $H_2O$:MeOH (4:1) containing HEPES buffer (10 mM, pH 7.4) solution at $\lambda_{ex}$=502 nm.
Figure 8:
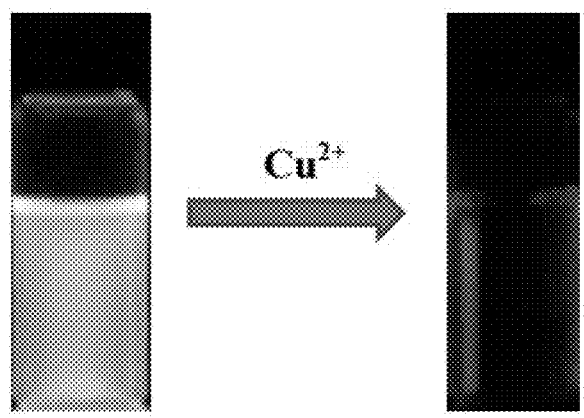
FIG. 8 is a representation of the fluorogenic change from green to colorless of fluorescein-N-methylimidazole conjugate based compound 1 (0.2 μM) upon the addition of $Cu(NO_3)_2$ in $H_2O$:MeOH (4:1) containing HEPES buffer (10 mM, pH 7.4) solution upon illumination at 365 nm.
Figure 9:
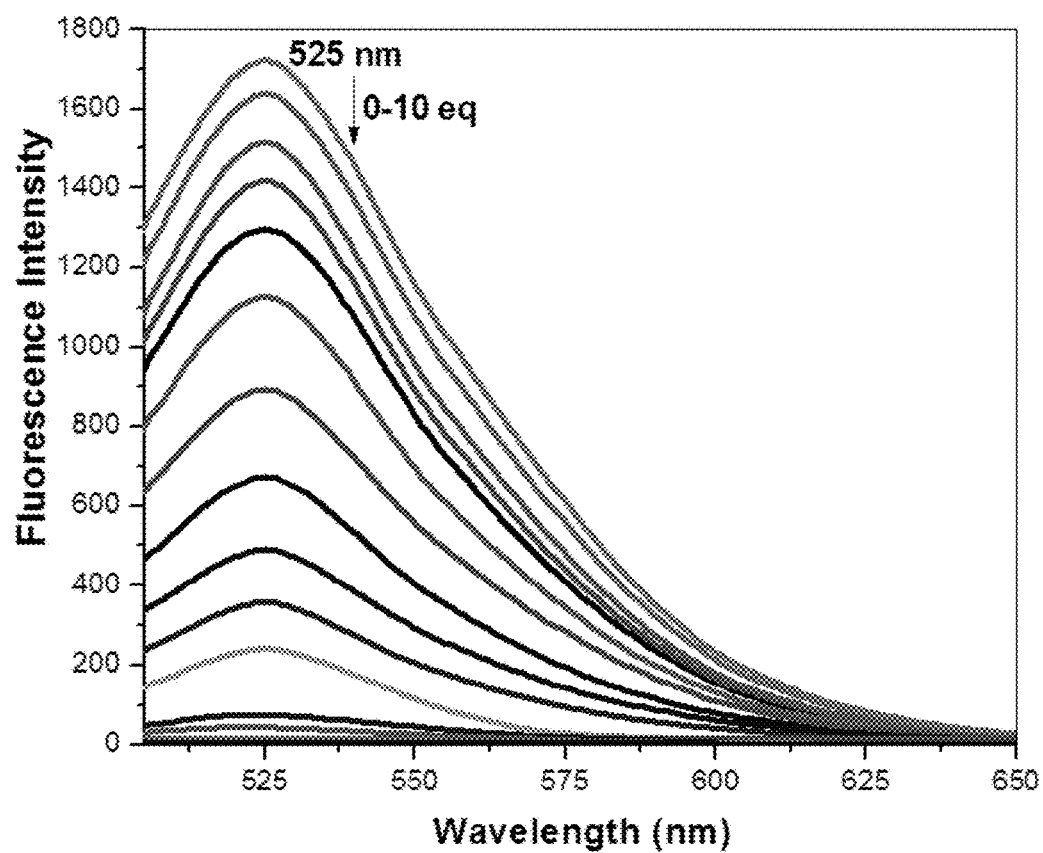
FIG. 9 is a fluorescence spectra of fluorescein-N-methylimidazole conjugate based compound 1 (0.2 μM) as a function of the addition of 0-10 molar equivalents of $Cu(NO_3)_2$ in $H_2O$:MeOH (4:1) containing HEPES buffer (10 mM, pH 7.4) solution with saturation occurring after the addition of 1 molar equivalent at $\lambda_{ex}$=502 nm.

All of the absorption and emission studies were carried out in mixed aqueous solutions of water and methanol (4:1) containing HEPES buffer (10 mM, pH 7.4) at a concentration of 20 μM and 0.2 μM respectively. Emission studies were carried out by addition of 10 equiv of various biologically and non-biologically relevant metal cations to an aqueous-MeOH (4:1) solution of compound 1 at a concentration level of 0.2 μM and their complexation abilities were studies by fluorescence. Compound 1 on excitation at 502 nm gave a strong fluorescence emission peak at 525 nm upon the addition of $Cu^{2+}$ the emission is completely quenched. Importantly, none of the other cations induced any such distinct emission shift or quenching (FIG. 7). In addition, the green fluorescence is completely quenched upon illumination at 365 nm (FIG. 8). Fluorescence titration of compound 1 with $Cu^{2+}$ was carried out in aqueous MeOH (4:1) solution at a concentration level of 0.2 μM. The addition of $Cu^{2+}$ to the solution of compound 1 caused a complete quenching of the fluorescent emission and the peak at 525 nm (Φ=0.32) is "switched off" when excited at 502 nm (FIG. 9).

The long wavelength of excitation (502 nm) and emission (525 nm) can prevent interference by autofluorescence from native cellular species, damage to living biological samples, and the influence of background fluorescence [Kobayashi, H.; Ogawa, M.; Alford, R.; Choyke, P. L.; Urano, Y. *Chem. Rev.* 2010, 110, 2620.; and Dujols, V.; Ford, F.; Czarnik, A. W. *J. Am. Chem. Soc.*, 1997, 119, 7386.; and Gunnlaugsson, T. Leonard, J. P. Senechal K. Harte, A. *J. Chem. Commun.*, 2004, 782.; and Klein, G. Kaufmann, D. Schurch S. Reymond, J.-L. *Chem. Commun.*, 2001, 561.—each incorporated herein by reference in its entirety]. The fluoroscein moiety is very weakly fluorescent in solution with no absorption in the visible region, due to the predominance of the ring-closed spirolactam form which is confirmed by $^{13}$C-NMR signals at 64.94 ppm and 64.47 ppm for compound 1 and compound 2 respectively.

Figure 10:
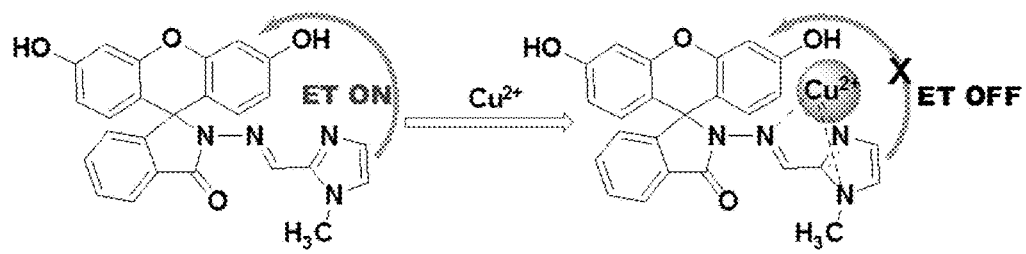
FIG. 10 is a proposed schematic representation for complexation of fluorescein-N-methylimidazole conjugate based chemosensor probe compound 1 with $Cu^{2+}$ ion.
Figure 11:
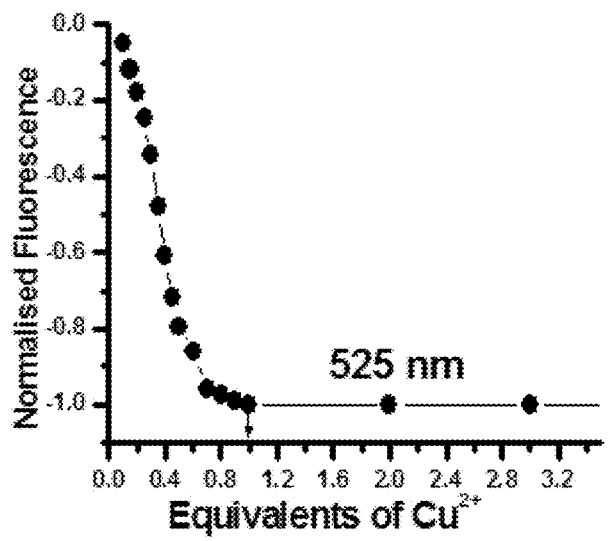
FIG. 11 is a molar ratio plot of normalized emission at 525 nm of fluorescein-N-methylimidazole conjugate based compound 1 (0.2 μM) upon the addition of 0-3 molar equivalents of $Cu(NO_3)_2$ in $H_2O$:MeOH (4:1) containing HEPES buffer (10 mM, pH 7.4) solution.

The green fluorescence in compound 1 arises due to the electron transfer (ET) from the nitrogen of the imidazole to the fluorescein ring (i.e. electron transfer is "switched on") (FIG. 10). As $Cu^{2+}$ is a paramagnetic cation, with open shell d-orbitals, the fluorescence quenching upon binding the $Cu^{2+}$ cation is presumably due to the electron transfer from the imidazole to the metal cation inhibiting the electron transfer between the fluorescein and imidazole (i.e. electron transfer is "switched off"). This provides a very fast and efficient non-radiative decay of the excited state [Wu, Q.; Anslyn, E. V. *J. Am. Chem. Soc.* 2004, 126, 14682.; and Gunnlaugsson, T.; Leonard, J. P.; Murray, N. S. *Org. Lett.* 2004, 6, 1557.; and Zeng, H. H.; Thompson, R. B.; Maliwal, B. P.; Fones, G. R.; Moffett, J. W.; Fierke, C. A. *Anal. Chem.* 2003, 75, 6807.; and Rurack, K. Spectrochim. Acta. A. 2001, 57, 2161.; and Kavallieratos, K.; Rosenberg, J. M.; Chen, W.-Z.; Ren, T. *J. Am. Chem. Soc.* 2005, 127, 6514.; and Zheng, Y.; Orbulescu, J.; Ji, X.; Andreopoulos, F. M.; Pham, S. M.; Leblanc, R. M. *J. Am. Chem. Soc.* 2003, 125, 2680.; and Quang, D. T.; Jung, H. S.; Yoon, J. H.; Lee, S. Y.; Kim, J. S. *Bull. Korean Chem. Soc.* 2007, 28, 682.—each incorporated herein by reference in its entirety]. The peak at 525 nm showed a linear diminution with an increase of $Cu^{2+}$ concentration when the ratio of $Cu^{2+}$ concentrations to compound 1 concentrations is less than or equal to 1:1. However, once the 1:1 ratio is reached higher $Cu^{2+}$ concentrations do not lead to any further emission enhancement (FIG. 11) [Connors, K. A. *Binding Constants: the Measurement of Molecular Complex Stability*. New York: Wiley, 1987; pp 21-101; 339-343.; and Forgues, S. F.; LeBris, M. T.; Gutte, J. P.; Valuer, B. *J. Phys. Chem.* 1988, 92, 6233.; and Thordarson, P. *Chem. Soc. Rev.* 2011.—each incorporated herein by reference in its entirety].

Example 6

Selectivity and Tolerance Studies

To evaluate the selectivity and tolerance of compound 1 for $Cu^{2+}$ over other metal cations, 10 equiv of the different metal cations were added to a 0.2 μM solution of compound 1. In the case of $Cu^{2+}$, the molecular fluorescence is quenched to a maximum level and therefore a high molecular sensitivity is attained. Nevertheless, there was no appreciable quenching with any other metal ions, as shown in FIG. 7. This selectivity is due to the fact that although transition metals do not differ much in size, they can establish interactions at very different energies, which can be used for discriminative purposes, especially for fluorescent sensing [Fabbrizzi, L.; Licchelli, M.; Pallavicini, P.; Parodi, L.; Taglietti, A. In *Transition Metals in Supramolecuar Chemistry*; Sauvage, J. P., Ed. Fluorescent sensors for and with transition metals; John Wiley & Sons Ltd: Chichester, 1999.—incorporated herein by reference in its entirety].

Figure 12:
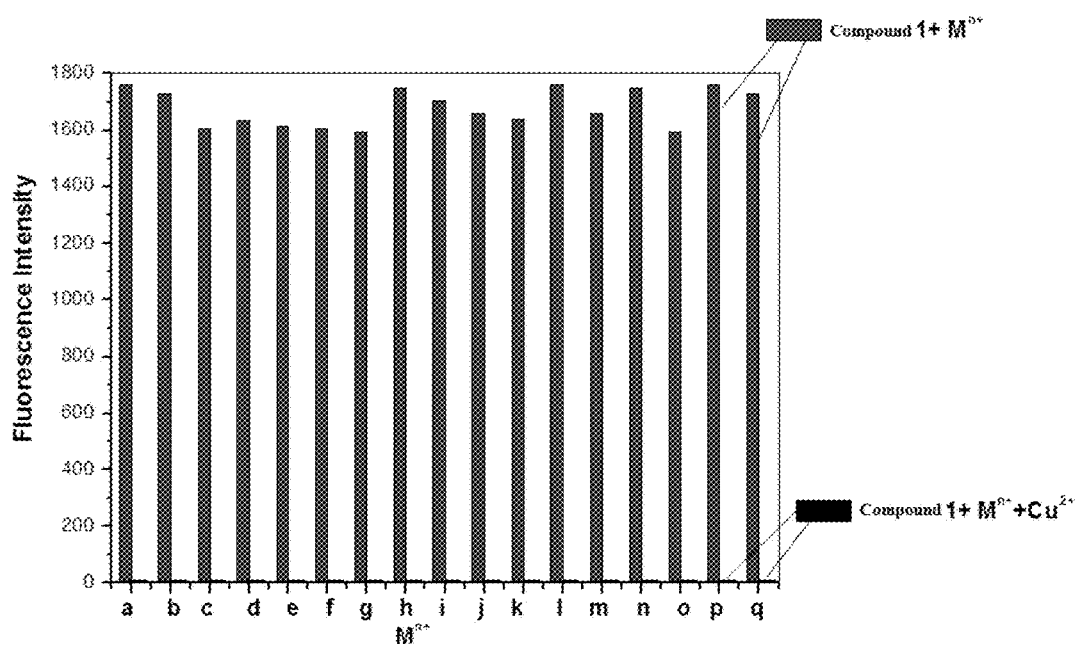
FIG. 12 is a graph demonstrating the metal ion selectivity of fluorescein-N-methylimidazole conjugate based compound 1 wherein bars indicate the fluorescence intensity (at 502 nm excitation and 525 nm emission) for various metal ions (10.0 equiv) added to compound 1 (0.2 μM) and $Cu^{2+}$ (1.0 equiv) in $H_2O$:MeOH (4:1) containing HEPES buffer (10 mM, pH 7.4) solution wherein (a) is compound 1, (b) is $Na^+$, (c) is $Co^{2+}$, (d) is $Ni^{2+}$, (e) is $Fe^{2+}$, (f) is $Fe^{3+}$, (g) is $Hg^{2+}$, (h) is $Rb^+$, (i) is $Cs^+$, (j) is $Cd^{2+}$, (k) is $Zn^{2+}$, (l) is $Mg^{2+}$, (111) is $Ca^{2+}$, (n) is $Ag^+$, (o) is $Pb^{2+}$, (p) is $K^+$, and (q) is $Al^{3+}$.
Figure 13:
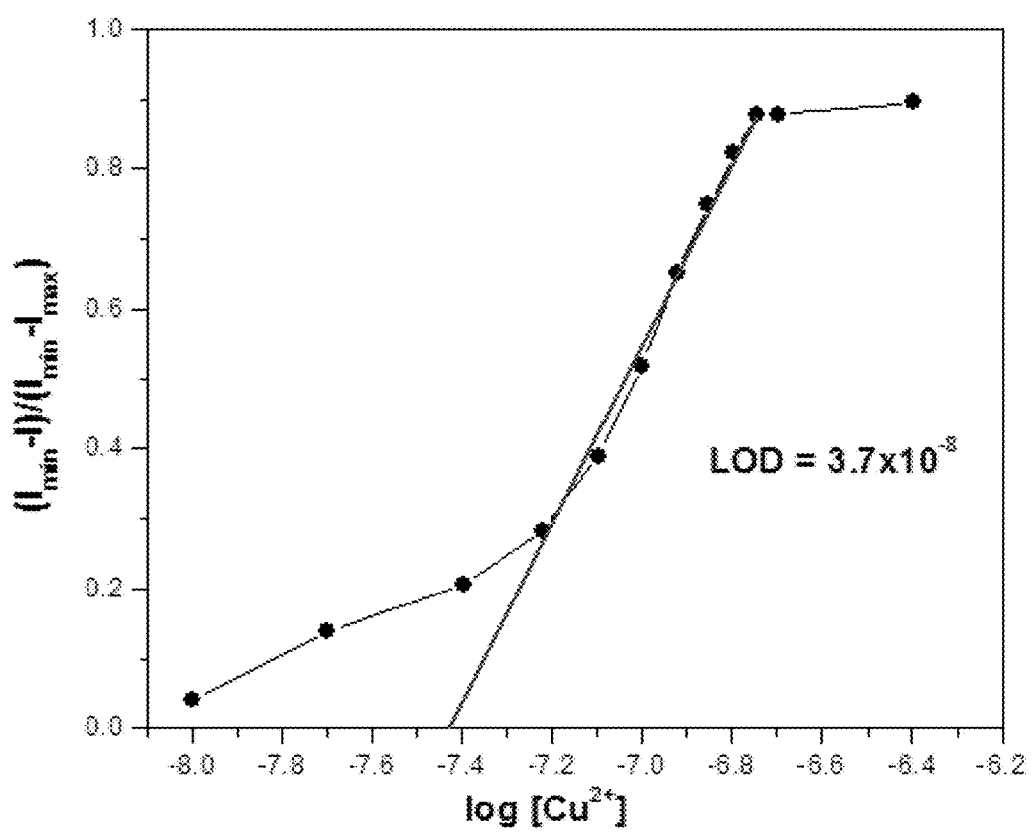
FIG. 13 is a plot of normalized fluorescence intensity of fluorescein-N-methylimidazole conjugate based compound 1 as a function of log [$Cu^{2+}$] in $H_2O$:MeOH (4:1) containing HEPES buffer (10 mM, pH 7.4) solution at $\lambda_{ex}$=502 nm.

This phenomenon is consistent with copper that occurs highest on the Irving-Williams series [Ci, Y. X.; Zhou, T. Z. *The Coordinated Complexes in Analytical Chemistry*; Peking University Press: Beijing, 1984.—incorporated herein by reference in its entirety]. Copper (II) has a particularly high thermodynamic affinity for the typical imino nitrogen, carbonyl group of the amide, and the imidazole nitrogen, with fast metal-to-ligand binding kinetics that are not possible with the other transition metal ions. Competitive binding experiments with different metal ions (10.0 equiv) and $Cu^{2+}$ ion (1.0 equiv) as shown in FIG. 12 demonstrated that different additional metal ions did not interfere with the quenching of compound 1 by the $Cu^{2+}$. It was also found that compound 1 shows a detection limit of 0.037 μM which is sufficient to sufficiently sense the $Cu^{2+}$ concentration in the blood system and in drinking water (FIG. 13).

Figure 14:
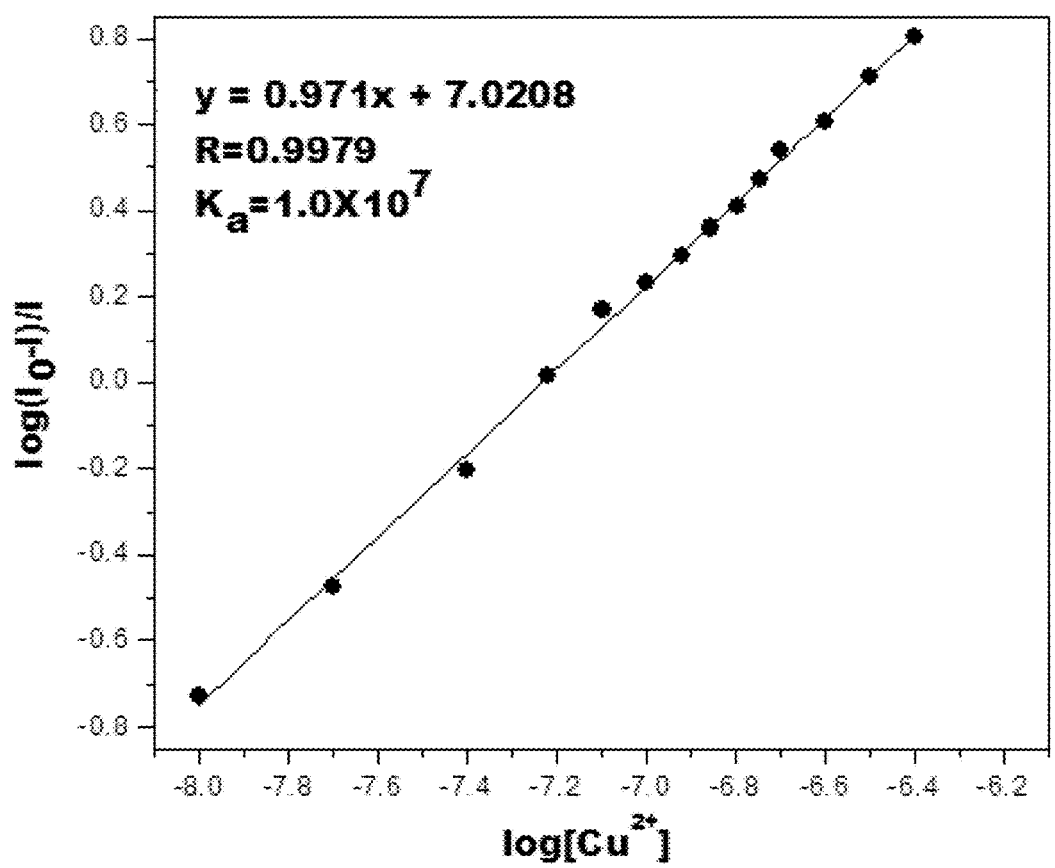
FIG. 14 is a Stern-Volmer plot of fluorescein-N-methylimidazole conjugate based compound 1 obtained by plotting log ($I_0$–I)/I as a function of log [$Cu^{2+}$] in $H_2O$:MeOH (4:1) containing HEPES buffer (10 mM, pH 7.4) solution at $\lambda_{ex}$=502 nm for compound 1.

The fluorescence titration spectra of compound 1 and compound 2 with $Cu^{2+}$ as well as the Job plot of compound 1 and the HR-Mass of the compound 1-$Cu^{2+}$ complex indicates that the binding of compound 1 with copper corresponds to a 1:1 stoichiometric complex formation in the aqueous MeOH (4:1) solution. Thus, it can be assumed that the quenching of the fluorescence of compound 1 by $Cu^{2+}$ ion is a static quenching mode due to the formation of a non-fluorescent complex in the ground state. In the case of a static quenching, the Stern-Volmer plot is linear and has been used to calculate the binding constant of compound 1 with $Cu^{2+}$. From the Stern-Volmer linear plot (FIG. 14) the binding constant of compound 1 with $Cu^{2+}$ was calculated to be $1.0 \times 10^7$ L·mol$^{-1}$ (error limits ≤10%).

Example 7

Effects of pH Studies

Figure 15:
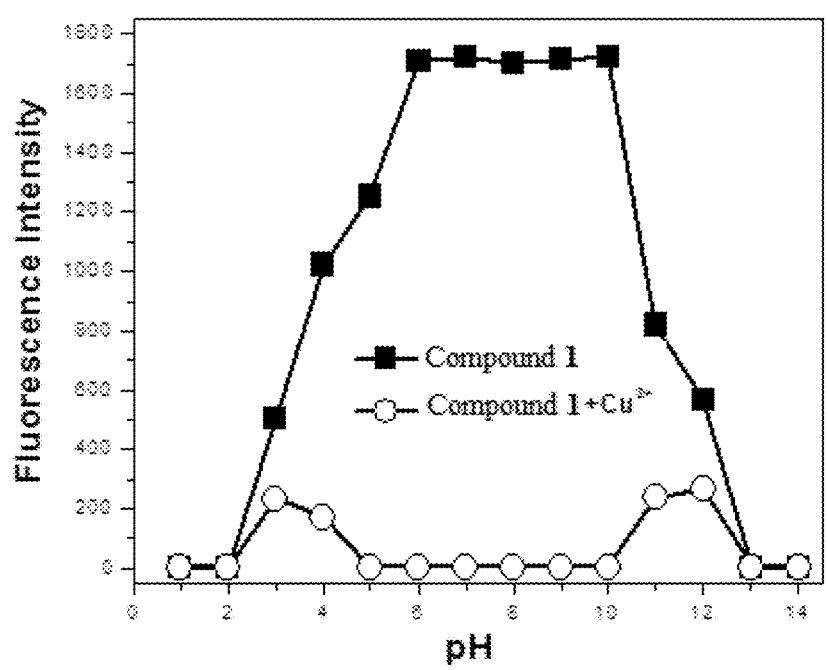
FIG. 15 is a plot demonstrating the effect of pH on the emission intensities of fluorescein-N-methylimidazole conjugate based compound 1 and its $Cu^{2+}$ complexes in $H_2O$:MeOH (4:1) containing HEPES buffer (10 mM, pH 7.4) solution at $\lambda_{ex}$=502 nm for compound 1.
Figure 16:
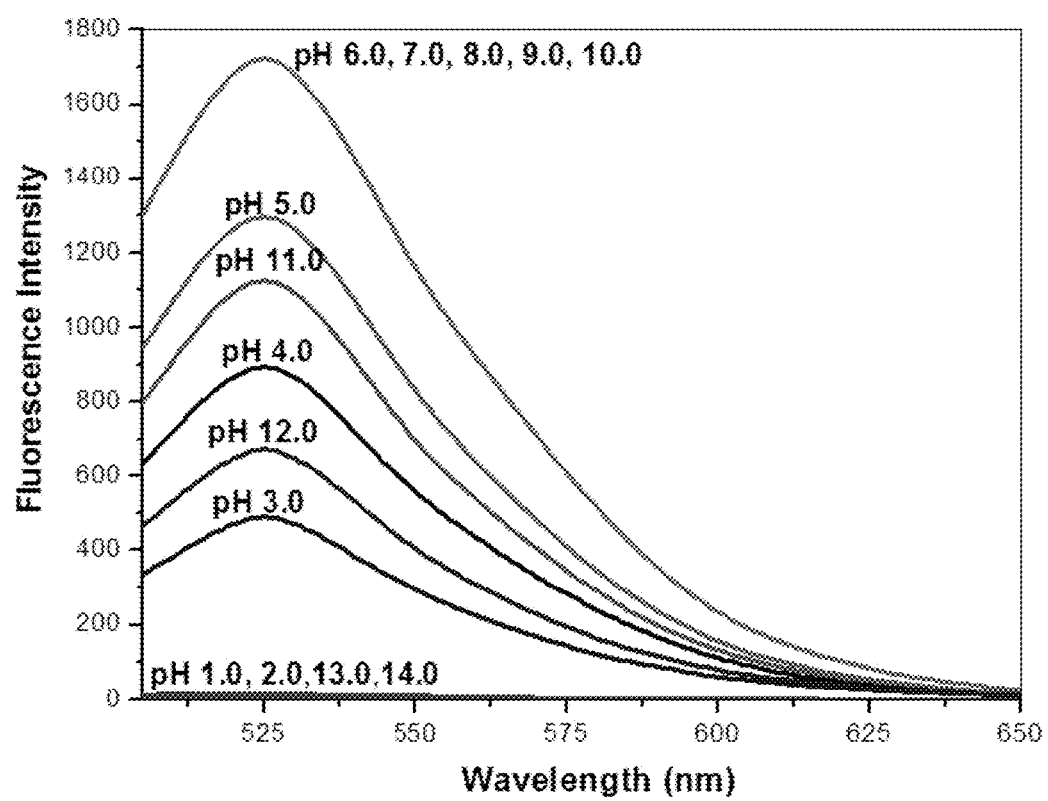
FIG. 16 is a fluorescence spectra demonstrating the effect of pH (1.0-14.0) on the fluorescence spectra of fluorescein-N-methylimidazole conjugate based compound 1 (0.2 µM) in $H_2O$:MeOH (4:1) containing HEPES buffer (10 mM, pH 7.4) solution at $\lambda_{ex}$=502 nm.
Figure 17:
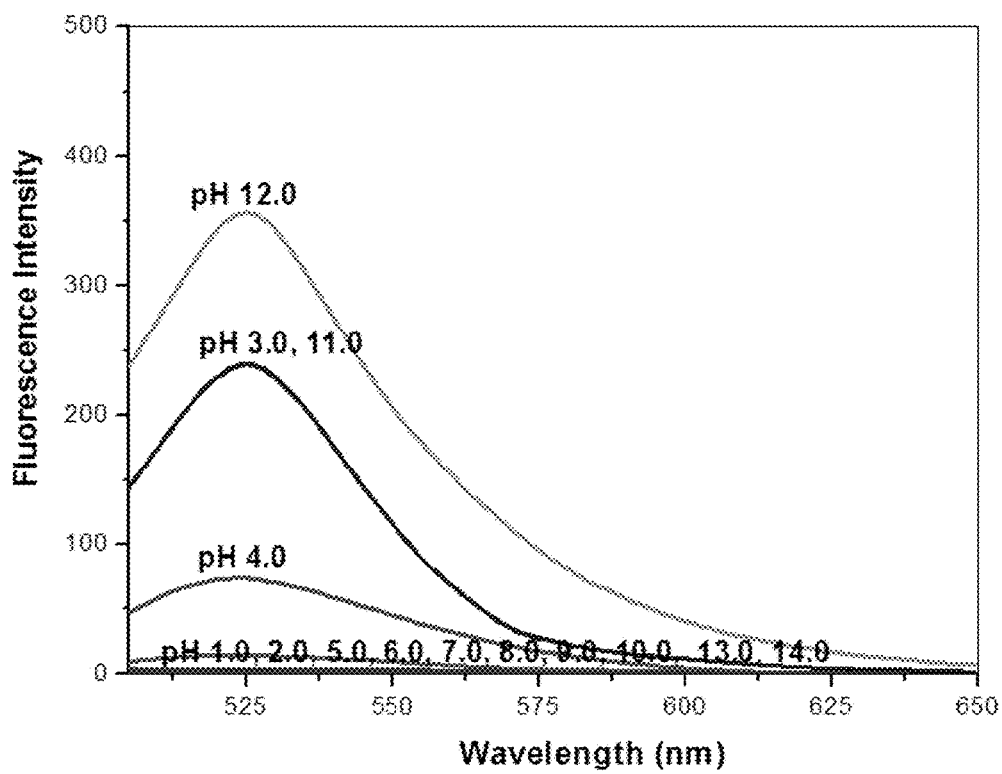
FIG. 17 is fluorescence spectra demonstrating the effect of pH (1.0-14.0) on the fluorescence spectra of fluorescein-N-methylimidazole conjugate based compound 1 (0.2 µM) in complex with $Cu^{2+}$ in $H_2O$:MeOH (4:1) containing HEPES buffer (10 mM, pH 7.4) solution at $\lambda_{ex}$=502 nm.

For the environmental and physiological applications of the chemosensors, the sensing should operate in a wide pH range. Thus, the effects of pH on the emission intensities of compound 1 in the absence and presence of $Cu^{2+}$ were investigated in the pH range from 2.0-12.0 (FIG. 15). Fluorescein exists in a closed, colorless and non-fluorescent spirocyclic form at pH levels classified as neutral and basic. In compound 1 decreasing pH protonates the nitrogen of the imidazole and thus inhibits the electron transfer to the fluorescein resulting in a decrease of fluorescence. At a pH of 5.0 compound 1 shows a maximum intensity the remains unchanged until pH values of at least 10.0. At higher pH (>10.0 in the case of compound 1) the fluorescence intensity is decreased due to the enhancement of negative charge density on the imidazole ring and formation of the phenolate of the fluorescein (FIG. 16 and FIG. 17). The effect of pH on the $Cu^{2+}$ complex of compound 1 shows that an increase in pH increase the amount of quenching, reaching its maximum at a pH of 5.0 after which it displays no pH sensitivity until a pH of 10.0. With further increases of pH, the fluorescence intensity of compound 1 and its $Cu^{2+}$ complexes becomes closer, likely due to the formation of a hydroxo-complex of $Cu^{2+}$ is favored under these conditions. Thus chemosensors such as compound 1 displayed virtually no physiological pH sensitivity and fluorescence "on-off" can be controlled by $Cu^{2+}$ ion binding within the pH range of 5.0 to 10.0.

Example 8

Chemical Reversibility Studies

Figure 18:
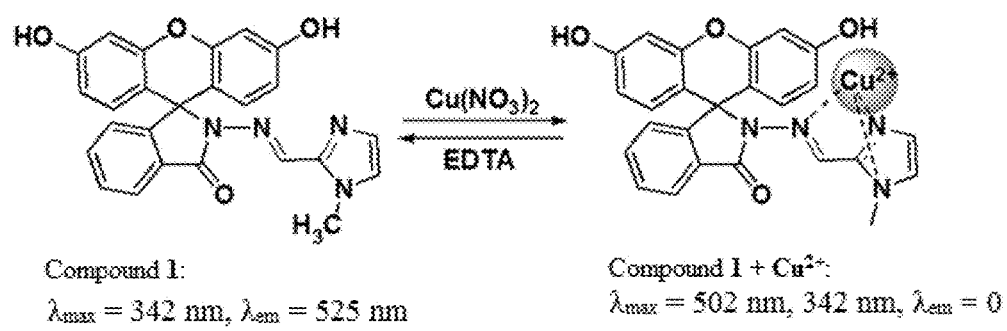
FIG. 18 is a proposed schematic representation for complexation of fluorescein-N-methylimidazole conjugate based chemosensor probe compound 1 with $Cu^{2+}$ ion as a chemically reversible process.

In addition, the chemical reversibility of $Cu^{2+}$ induced fluorescence variation of compound 1 in the $H_2O$:MeOH (4:1) containing HEPES buffer (10 mM, pH 7.4) solution was investigated. When an aqueous solution of EDTA (2.0 μM) was added to the complexed solution of compound 1 (0.2 μM) and $Cu^{2+}$ (2.0 μM) the fluorescence of the solution at 525 nm instantly recovered. Simultaneously, the solution color clearly reverted turning colorless from light yellow with the disappearance of the peak at 502. This result indicates that the introduction of chelator EDTA can immediately capture the compound 1 bound $Cu^{2+}$, and furthermore that the binding of compound 1 with $Cu^{e^+}$ is a chemically reversible process (FIG. 18). Thus, compound 1 could serve as a potential recyclable component in sensing materials.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A fluorescent Schiff base of formula (I):

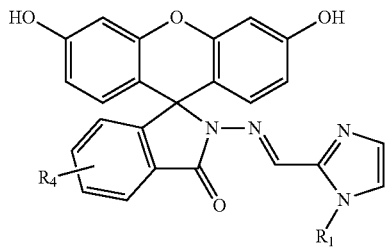

or a salt, solvate, tautomer, or stereoisomer thereof;
wherein $R_1$ is an optionally substituted alkyl, optionally substituted cycloalkyl, or optionally substituted aryl;
$R_2$ an $R_3$ are independently —OH, —$NH_2$, —$OR_5$, —$NR_5R_5$;
$R_4$ is —H, —F, —Cl, —Br, —CN, —OH, —$OR_5$, —$NO_2$, —$NH_2$, —$NHR_5$, —$NR_5R_5$; and
each $R_5$ is independently an optionally substituted alkyl, optionally substituted cycloalkyl, or optionally substituted aryl.

2. The fluorescent Schiff base of claim 1, wherein the compound of formula (I) is

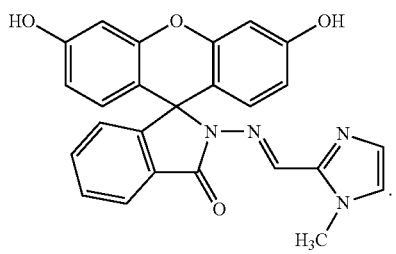 [SMILES: Cn1ccnc1/C=N/N1C(=O)c2ccccc2C12c1ccc(O)cc1Oc1cc(O)ccc12]

3. The fluorescent Schiff base of claim 1, which has a fluorescence with an emission peak centered at 515-535 nm at an excitation wavelength of 490-510 nm and which has an ultraviolet visible absorption with an absorption peak centered at 330-350 nm.

4. The fluorescent Schiff base of claim 3, wherein upon binding with one or more $Cu^{2+}$ ions the ultraviolet visible absorption with an absorption peak centered at 330-350 nm decreases in intensity synchronously to an increasing ultraviolet visible absorption with an absorption peak centered at 490-510 nm.

5. The fluorescent Schiff base of claim 3, wherein upon binding with one or more $Cu^{2+}$ ions the fluorescence with an emission peak centered at 515-535 nm at an excitation wavelength of 490-510 nm is quenched and/or inhibited.

6. The fluorescent Schiff base of claim 1, which binds with one or more $Cu^{2+}$ ions by monodentate coordination, bidentate chelation or tridentate chelation to the $Cu^{2+}$ ion to form a metal ion complex.

7. The fluorescent Schiff base of claim 1, which has a $Cu^{2+}$ binding constant in the range of $0.5 \times 10^7$ L·$mol^{-1}$ to $1.5 \times 10^7$ L·$mol^{-1}$ as calculated from fluorescence titration.

8. A process for producing the fluorescent Schiff base of claim 1, comprising:
refluxing a fluorescein or rhodamine based compound with hydrazine to form a fluorescein or rhodamine based hydrazide; and
refluxing the fluorescein or rhodamine based hydrazide with a N-alkylimidazole-2-carboxaldehyde to form the fluorescent Schiff base.

9. A method for detecting and quantifying $Cu^{2+}$ ions in a fluid sample, comprising:
contacting the fluid sample with the fluorescent Schiff base of claim 1; and
measuring fluorescence emission at 515-535 nm with an excitation wavelength of 490-510 nm to determine a concentration of $Cu^{2+}$ ions in the fluid sample;
wherein during the contacting the fluorescent Schiff base binds to the $Cu^{2+}$ ions at a molar ratio of 1:1 and quenches and/or inhibits the fluorescence emission.

10. The method of claim 9, wherein the binding of the fluorescent Schiff base to the $Cu^{2+}$ ions further results in an ultraviolet visible absorption with an absorption peak centered at 490-510 nm.

11. The method of claim 9, wherein the binding of the fluorescent Schiff base to the $Cu^{2+}$ ions is a chemically reversible process and the introduction of a chelator restores the fluorescence emission centered at 515-535 nm.

12. The method of claim 9, further comprising measuring the fluorescence emission of a plurality of calibration fluid samples to obtain a calibration curve, wherein the plurality of calibration fluid samples comprise different known concentrations of $Cu^{2+}$ ions.

13. The method of claim 9, wherein the fluid sample has a pH in the range of 4.5 to 10.5.

14. The method of claim 9, wherein the fluorescent Schiff base is present at a concentration of 0.1-25 μM during the measuring.

15. The method of claim 9, which has a $Cu^{2+}$ detection lower limit of 0.01-0.05 μM without interference from one or more additional metal ions.

16. The method of claim 15, wherein the one or more additional metal ions are selected from the group consisting of $Ag^{2+}$, $Pb^{2+}$, $Ca^{2+}$, $Ni^{2+}$, $Co^{2+}$, $K^+$, $Zn^{2+}$, $Al^{3+}$, $Fe^{3+}$, $Fe^{2+}$, $Na^+$, $Cd^{2+}$, $Mg^{2+}$, $Hg^{2+}$, $Rb^+$, and $Cs^+$.

17. The method of claim 9, wherein the fluid sample comprises greater than 10% v/v of water as a solvent and is at least one selected from the group consisting of contaminated water, a consumable good, and a bodily fluid.

18. The fluorescent Schiff base of claim 1 or a salt or solvate thereof.

19. A fluorescent probe comprising the fluorescent Schiff base of claim 1.

20. The fluorescent Schiff base of claim 1, where $R_2$ is —$OR_5$.

* * * * *